US008173422B2

(12) United States Patent
Otte et al.

(10) Patent No.: US 8,173,422 B2
(45) Date of Patent: May 8, 2012

(54) METHOD FOR IMPROVING PROTEIN PRODUCTION

(75) Inventors: Arie Pieter Otte, Amersfoort (NL); Henricus Johannes Maria Van Blokland, Wijdewormer (NL)

(73) Assignee: Chromagenics B.V., Leiden (NL)

(*) Notice: Subject to any disclaimer, the term of this patent is extended or adjusted under 35 U.S.C. 154(b) by 872 days.

(21) Appl. No.: 12/218,128

(22) Filed: Jul. 11, 2008

(65) Prior Publication Data
US 2009/0011468 A1 Jan. 8, 2009

Related U.S. Application Data

(63) Continuation of application No. 11/157,193, filed on Jun. 20, 2005, now Pat. No. 7,413,896, which is a continuation of application No. PCT/NL03/00850, filed on Dec. 2, 2003.

(30) Foreign Application Priority Data
Dec. 18, 2002 (EP) .................................. 02080347

(51) Int. Cl.
C12N 15/00 (2006.01)
C12N 15/63 (2006.01)
C07H 21/04 (2006.01)
A01K 67/00 (2006.01)

(52) U.S. Cl. ..................... 435/320.1; 435/455; 536/24.1

(58) Field of Classification Search ........................ None
See application file for complete search history.

(56) References Cited

U.S. PATENT DOCUMENTS

| | | | |
|---|---|---|---|
| 5,610,053 A | 3/1997 | Chung et al. | |
| 5,658,763 A | 8/1997 | Dorai et al. | |
| 5,773,695 A | 6/1998 | Thompson et al. | |
| 5,888,809 A | 3/1999 | Allison | |
| 6,395,549 B1 | 5/2002 | Tuan et al. | |
| 6,521,419 B1 | 2/2003 | Koduri et al. | |
| 6,586,205 B1 | 7/2003 | Glucksmann et al. | |
| 6,787,321 B1* | 9/2004 | Tetsu et al. ..................... 435/7.2 | |
| 6,872,524 B1 | 3/2005 | Otte | |
| 7,109,029 B2 | 9/2006 | Clarke et al. | |
| 7,192,741 B2 | 3/2007 | Otte et al. | |
| 7,413,896 B2* | 8/2008 | Otte et al. ..................... 435/320.1 | |
| 2003/0138908 A1 | 7/2003 | Koduri et al. | |
| 2003/0166042 A1 | 9/2003 | Glucksmann et al. | |
| 2003/0199468 A1 | 10/2003 | Otte et al. | |
| 2005/0106609 A1 | 5/2005 | Otte | |
| 2006/0003416 A1 | 1/2006 | Otte et al. | |
| 2006/0141577 A1 | 6/2006 | Otte et al. | |
| 2006/0172382 A1 | 8/2006 | Otte et al. | |
| 2006/0195935 A1 | 8/2006 | Otte et al. | |
| 2006/0263882 A1 | 11/2006 | Fazio et al. | |
| 2008/0085537 A1 | 4/2008 | Otte et al. | |
| 2008/0227151 A1 | 9/2008 | Otte et al. | |
| 2009/0098601 A1 | 4/2009 | Otte et al. | |
| 2010/0136616 A1 | 6/2010 | Otte et al. | |
| 2010/0190207 A1 | 7/2010 | Otte et al. | |
| 2011/0014655 A1 | 1/2011 | Otte et al. | |

FOREIGN PATENT DOCUMENTS

| | | |
|---|---|---|
| EP | 1 273 666 | 1/2003 |
| WO | WO 96/04390 | 2/1996 |
| WO | WO 97/27207 | 7/1997 |
| WO | WO 98/11207 | 3/1998 |
| WO | WO 98/49289 | 11/1998 |
| WO | WO 00/05393 | 2/2000 |
| WO | WO 00/09749 | 2/2000 |
| WO | WO 00/17337 | 3/2000 |
| WO | WO 00/23606 | 4/2000 |
| WO | WO 01/59117 | 8/2001 |
| WO | WO 01/59118 | 8/2001 |
| WO | WO 02/24930 A2 | 3/2002 |
| WO | WO 03/004704 | 1/2003 |
| WO | WO 2004/055215 A1 | 7/2004 |
| WO | WO 2004/056986 A2 | 7/2004 |

OTHER PUBLICATIONS

Aranda et al., Definition of Transcriptional Pause Elements in Fission Yeast, Molecular and Cellular Biology, Feb. 1999, pp. 1251-1261, vol. 19, No. 2.
Auten et al., "Effect of Scaffold Attachment Region on Transgene Expression in Retrovirus Vector-Transduced Primary T cells and Macrophages," Human Gene Therapy, May 20, 1999, pp. 1389-1399, vol. 10, No. 8.
Bell et al., Insulators and Boundaries: Versatile Regulatory Elements in the Eukaryotic Genome, Science, pp. 447-450, vol. 291, No. 5503.
Burgess-Beusse et al., The insulation of genes from external enhancers and silencing chromatin, PNAS, Dec. 10, 2002, pp. 16433-16437, vol. 99, Suppl. 4.
Chan et al., p300-CBP proteins: HATs for transcriptional bridges and scaffolds, Journal of Cell Science, 2001, pp. 2363-2373, vol. 114.
Chung et al., A 5' Element of the Chicken Beta-Globin Domain Serves as an Insulator in Human Erythroid Cells and Protects against Position Effect in *Drosophila*, Aug. 13, 1993, Cell, pp. 505-514, vol. 74.

(Continued)

Primary Examiner — Quang Nguyen
(74) Attorney, Agent, or Firm — TraskBritt

(57) ABSTRACT

The present invention relates to the production of proteins in a cell or host cell. The invention uses a TRAnscription Pause (TRAP) sequence to enhance a protein expression characteristic of a protein expression unit. The TRAP sequence is thought to prevent, at least in part, formation of antisense RNA or to, at least in part, prevent transcription to enter the protein expression unit. In one embodiment, the invention provides a method for expression of at least one protein of interest in a cell comprising providing the cell with at least one protein expression unit that comprises a promoter functionally linked to an open reading frame encoding at least one protein of interest, characterized in that the protein expression unit further comprises at least one TRAP sequence and wherein the TRAP sequence is functionally located downstream of the open reading frame and at least in part prevents formation of antisense RNA. In another embodiment, the TRAP sequence is functionally located upstream of the promoter and at least in part prevents transcription to enter the expression unit. Preferably, the expression protein unit further comprises at least one STabilizing Anti-Repressor sequence.

23 Claims, 8 Drawing Sheets

OTHER PUBLICATIONS

Eggermont et al., Poly(A) signals and transcriptional pause sites combine to prevent interference between RNA polymerase II promoters, The EMBO Journal, 1993, pp. 2539-2548, vol. 12, No. 6.

Emery et al., A chromatin insulator protects retrovirus vectors from chromosomal position effects, Proceedings of the National Academy of Sciences of USA, Aug. 1, 2000, pp. 9150-9155, vol. 97, No. 16.

Farrell et al., Conserved CTCF Insulator Elements Flank the Mouse and Human Beta-Globin Loci, Molecular and Cellular Biology, Jun. 2002, pp. 3820-3831, vol. 22. No. 11.

Han et al., "Matrix attachment regions (MARs) enhance transformation frequency and transgene expression in poplar," Transgenic Research, 1997, pp. 415-420, vol. 6.

Johnson et al., Requirements for utilization of CREB binding protein by hypersensitive site two of the Beta-globin locus control region, Nucleic Acids Research 2002, pp. 1522-1530, vol. 30, No. 7.

Kellum et al., A Group of scs Elements Function as Domain Boundaries in an Enhancer-Blocking Assay, Molecular and Cellular Biology, May 1992, pp. 2424-2431, vol. 12, No. 5.

Kwaks et al., Identification of anti-repressor elements that confer high stable protein in production in mammalian cells, Nature Biotechnology, May 20, 2003, pp. 553-558, vol. 21, No. 5.

Maniatis et al., Recognition Sequences of Repressor and Polymerase in the Operators of Bacteriophage Lambda, Cell, Jun. 1975, pp. 109-113, vol. 5.

Martinez-Balbas et al., The acetyltransferase activity of CBP stimulates transcription, The EMBO Journal, 1998, pp. 2886-2893, vol. 17, No. 10.

Mielke et al., "Stabilized, long-term expression of heterodimeric proteins from tricistronic mRNA," Gene, Aug. 22, 2000, pp. 1-8, vol. 254, No. 1-2.

Migliaccio et al., "Stable and unstable transgene integration sites in the human genome: extinction of the Green fluorescent Protein transgene in K562 cells," Gene, Oct. 3, 2000, pp. 197-214, vol. 256, No. 1-2.

Pile et al., GAGA Factor-dependent Transcription and Establishment of DNase Hypersensitivity are Independent and Unrelated Events in Vivo, J. of Biological Chemistry, Jan. 14, 2000, pp. 1398-1404, vol. 275, No. 2.

Reik et al., Biotechnologies and therapeutics: Chromatin as a target, Current Opinion in Genetics & Development, 2002, pp. 233-242, vol. 12.

Seum et al., A GAL4-HPI fusion protein targeted near heterochromatin promotes gene silencing, Chromosoma, 2000, pp. 453-459, vol. 109.

Sigrist et al., Chromatin Insulator Elements Black the Silencing of a Target Gene by the *Drosophila* Polycomb Response Element (PRE) but Allow trans Interactions Between PREs on Different Chromosomes, Genetics, Sep. 1997, pp. 209-211, vol. 147, No. 1.

Van Der Vlag et al., Transcription Repression Mediated by Polycomb Group Proteins and Other Chromatin-associated Repressors is Selectively Blocked by Insulators, Journal of Biological Chemistry, Jan. 7, 2000, pp. 697-704, vol. 275, No. 1.

West et al., Insulators: many functions, many mechanisms, Genes and Development, Feb. 1, 2002, pp. 271-288, vol. 16, No. 3.

Youn et al., An Intronic Silencer of the Mouse Perforin Gene, Mol. Cells., pp. 61-68, vol. 33, No. 1.

* cited by examiner

Loss of gene expression constructs
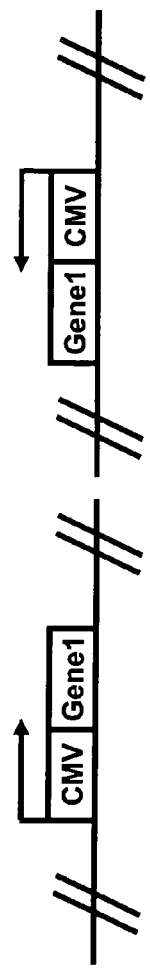
FIG. 1A
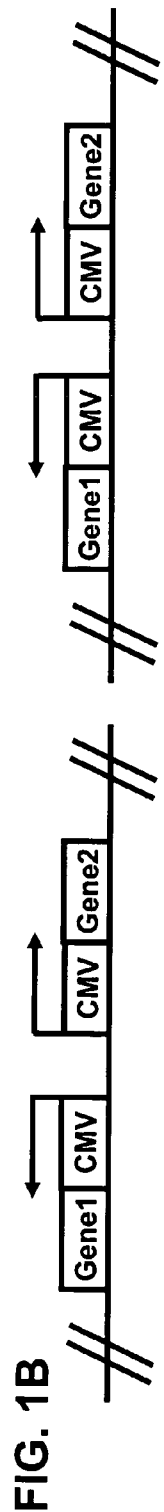
FIG. 1B
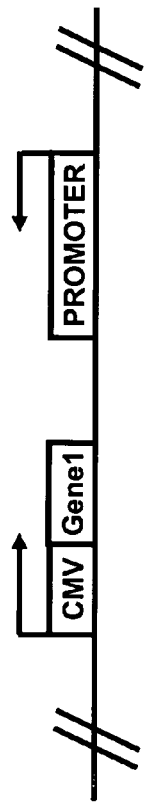
FIG. 1C
FIG. 1

SEQUENCE LISTING

<160> NUMBER OF SEQ ID NOS: 34

<210> SEQ ID NO 1
<211> LENGTH: 22
<212> TYPE: DNA
<213> ORGANISM: Artificial Sequence
<220> FEATURE:
<223> OTHER INFORMATION: oligo STOP 1

<400> SEQUENCE: 1
ctagctaagt aagtaagctt gg                                              22

<210> SEQ ID NO 2
<211> LENGTH: 17
<212> TYPE: DNA
<213> ORGANISM: Artificial Sequence
<220> FEATURE:
<223> OTHER INFORMATION: oligo STOP 2

<400> SEQUENCE: 2
aattccaagc ttactta                                                    17

<210> SEQ ID NO 3
<211> LENGTH: 24
<212> TYPE: DNA
<213> ORGANISM: Artificial Sequence
<220> FEATURE:
<223> OTHER INFORMATION: oligo BamHI-BglII-AscI

<400> SEQUENCE: 3
ttaaggatcc agatctggcg cgcc                                            24

<210> SEQ ID NO 4
<211> LENGTH: 24
<212> TYPE: DNA
<213> ORGANISM: Artificial Sequence
<220> FEATURE:
<223> OTHER INFORMATION: oligo AscI-BglII-BamHI

<400> SEQUENCE: 4
ttaaggcgcg ccagatctgg atcc                                            24

<210> SEQ ID NO 5
<211> LENGTH: 22
<212> TYPE: DNA
<213> ORGANISM: Artificial Sequence
<220> FEATURE:
<223> OTHER INFORMATION: oligo NotI-BclI-EV

<400> SEQUENCE: 5
ggccgctgat cagatatcgc gg                                              22

<210> SEQ ID NO 6
<211> LENGTH: 22
<212> TYPE: DNA
<213> ORGANISM: Artificial Sequence
<220> FEATURE:
<223> OTHER INFORMATION: oligo NheI-EcoRV-BclI

<400> SEQUENCE: 6
ctagccgcga tatctgatca gc                                              22

<210> SEQ ID NO 7
<211> LENGTH: 49
<212> TYPE: DNA

<213> ORGANISM: Artificial Sequence
<220> FEATURE:
<223> OTHER INFORMATION: synthetic polyA (SPA) sequence

<400> SEQUENCE: 7

```
aataaaagat ccttatttc actagttctg tgtgttggtt ttttgtgtg                    49
```

<210> SEQ ID NO 8
<211> LENGTH: 92
<212> TYPE: DNA
<213> ORGANISM: Artificial Sequence
<220> FEATURE:
<223> OTHER INFORMATION: sequence of pausing signal from the human
      alpha2 globin gene

<400> SEQUENCE: 8

```
aacatacgct ctccatcaaa acaaaacgaa acaaaacaaa ctagcaaaat aggctgtccc       60
cagtgcaagt gcaggtgcca gaacatttct ct                                    92
```

<210> SEQ ID NO 9
<211> LENGTH: 26
<212> TYPE: DNA
<213> ORGANISM: Artificial Sequence
<220> FEATURE:
<223> OTHER INFORMATION: oligonucleotide

<400> SEQUENCE: 9

```
gtacggatat cagatctta attaag                                            26
```

<210> SEQ ID NO 10
<211> LENGTH: 24
<212> TYPE: DNA
<213> ORGANISM: Artificial Sequence
<220> FEATURE:
<223> OTHER INFORMATION: oligonucleotide

<400> SEQUENCE: 10

```
gtaccttaat taaagatctg atat                                             24
```

<210> SEQ ID NO 11
<211> LENGTH: 52
<212> TYPE: DNA
<213> ORGANISM: Artificial Sequence
<220> FEATURE:
<223> OTHER INFORMATION: primer

<400> SEQUENCE: 11

```
gatcagatct ggcgcgccat ttaaatcgtc tcgcgcgttt cggtgatgac gg              52
```

<210> SEQ ID NO 12
<211> LENGTH: 41
<212> TYPE: DNA
<213> ORGANISM: Artificial Sequence
<220> FEATURE:
<223> OTHER INFORMATION: primer

<400> SEQUENCE: 12

```
aggcggatcc gaatgtattt agaaaaataa acaaataggg g                          41
```

<210> SEQ ID NO 13
<211> LENGTH: 36
<212> TYPE: DNA
<213> ORGANISM: Artificial Sequence
<220> FEATURE:
<223> OTHER INFORMATION: primer

<400> SEQUENCE: 13

```
gatcggatcc ttcgaaatgg ccaagttgac cagtgc                                 36
```

```
<210> SEQ ID NO 14
<211> LENGTH: 32
<212> TYPE: DNA
<213> ORGANISM: Artificial Sequence
<220> FEATURE:
<223> OTHER INFORMATION: primer

<400> SEQUENCE: 14
aggcgcggcc gcaattctca gtcctgctcc tc                                     32
```

```
<210> SEQ ID NO 15
<211> LENGTH: 31
<212> TYPE: DNA
<213> ORGANISM: Artificial Sequence
<220> FEATURE:
<223> OTHER INFORMATION: primer

<400> SEQUENCE: 15
gatcgaattc tcgcgacttc gcccaccatg c                                      31
```

```
<210> SEQ ID NO 16
<211> LENGTH: 47
<212> TYPE: DNA
<213> ORGANISM: Artificial Sequence
<220> FEATURE:
<223> OTHER INFORMATION: primer

<400> SEQUENCE: 16
aggcgaattc accggtgttt aaactcatgt ctgctcgaag cggccgg                     47
```

```
<210> SEQ ID NO 17
<211> LENGTH: 31
<212> TYPE: DNA
<213> ORGANISM: Artificial Sequence
<220> FEATURE:
<223> OTHER INFORMATION: primer

<400> SEQUENCE: 17
gatcgaattc atggtgagca agggcgagga g                                      31
```

```
<210> SEQ ID NO 18
<211> LENGTH: 40
<212> TYPE: DNA
<213> ORGANISM: Artificial Sequence
<220> FEATURE:
<223> OTHER INFORMATION: primer

<400> SEQUENCE: 18
aggcacgcgt gttaacctac acattgatcc tagcagaagc                             40
```

```
<210> SEQ ID NO 19
<211> LENGTH: 43
<212> TYPE: DNA
<213> ORGANISM: Artificial Sequence
<220> FEATURE:
<223> OTHER INFORMATION: primer

<400> SEQUENCE: 19
gatcatttaa atgtcgacct gaattgctat gtttagtgag ttg                         43
```

```
<210> SEQ ID NO 20
<211> LENGTH: 25
<212> TYPE: DNA
<213> ORGANISM: Artificial Sequence
```

<220> FEATURE:
<223> OTHER INFORMATION: primer

<400> SEQUENCE: 20
gatcgtcgac gtttggctga tcggc                                          25

<210> SEQ ID NO 21
<211> LENGTH: 32
<212> TYPE: DNA
<213> ORGANISM: Artificial Sequence
<220> FEATURE:
<223> OTHER INFORMATION: primer

<400> SEQUENCE: 21
gatcttaatt aaccaagctt gcatgcctgc ag                                  32

<210> SEQ ID NO 22
<211> LENGTH: 30
<212> TYPE: DNA
<213> ORGANISM: Artificial Sequence
<220> FEATURE:
<223> OTHER INFORMATION: primer

<400> SEQUENCE: 22
aggcgatatc gcgcgagacg atttaaatgg                                     30

<210> SEQ ID NO 23
<211> LENGTH: 2398
<212> TYPE: DNA
<213> ORGANISM: Artificial Sequence
<220> FEATURE:
<223> OTHER INFORMATION: lambda fragment 35711-38103

<400> SEQUENCE: 23
agatctgaat tgctatgttt agtgagttgt atctatttat ttttcaataa atacaattgg      60
ttatgtgttt tgggggcgat cgtgaggcaa agaaaacccg cgcgctgaggc cgggttattc    120 ttgttctctg gtcaaattat atagttggaa acaaggatg catatatgaa tgaacgatgc     180
agaggcaatg ccgatggcga tagtgggtat catgtagccg cttatgctgg aaagaagcaa    240
taacccgcag aaaaacaaag ctccaagctc aacaaaacta agggcataga caataactac    300
cgatgtcata tacccatact ctctaatctt ggccagtcgg cgcgttctgc ttccgattag    360
aaacgtcaag gcagcaatca ggattgcaat catggttcct gcatatgatg acaatgtcgc    420
cccaagacca tctctatgag ctgaaaaaga acaccagga atgtagtggc ggaaaaggag    480
atagcaaatg cttacgataa cgtaaggaat tattactatg taaacaccag gcatgattct    540
gttccgcata attactcctg ataattaatc cttaactttg cccacctgcc ttttaaaaca    600
ttccagtata tcacttttca ttcttgcgta gcaatatgcc atctcttcag ctatctcagc    660
attggtgacc ttgttcagag cgctgagag atggccttt tctgatagat aatgttctgt     720
taaaatatct ccggcctcat cttttgcccg caggctaatg tctgaaaatt gaggtgacgg    780
gttaaaaata atatccttgg caaccttttt tatatccctt ttaaattttg gcttaatgac    840
tatatccaat gagtcaaaaa gctccccttc aatatctgtt gccctaagga cctttaatat    900
atcgccaaat acaggtagct tggcttctac cttcaccgtt gttcggccga tgaaatgcat    960
atgcataaca tcgtctttgg tggttcccct catcagtggc tctatctgaa cgcgctctcc   1020
actgcttaat gacattcctt tcccgattaa aaaatctgtc agatcggatg tggtcggccc   1080 gaaacagtt ctggcaaaac caatggtgtc gccttcaaca acaaaaaag atgggaatcc    1140 caatgattcg tcatctgcga ggctgttctt aatatcttca actgaagctt tagagcgatt   1200

```
tatcttctga accagactct tgtcatttgt tttggtaaag agaaaagttt ttccatcgat    1260
tttatgaata tacaaataat tggagccaac ctgcaggtga tgattatcag ccagcagaga    1320
attaaggaaa acagacaggt ttattgagcg cttatctttc cctttatttt tgctgcggta    1380
agtcgcataa aaccattct tcataattca atccatttac tatgttatgt tctgagggga    1440
gtgaaaattc ccctaattcg atgaagattc ttgctcaatt gttatcagct atgcgccgac    1500
cagaacacct tgccgatcag ccaaacgtct cttcaggcca ctgactagcg ataactttcc    1560
ccacaacgga acaactctca ttgcatggga tcattgggta ctgtgggttt agtggttgta    1620
aaaacacctg accgctatcc ctgatcagtt tcttgaaggt aaactcatca cccccaagtc    1680
tggctatgca gaaatcacct ggctcaacag cctgctcagg gtcaacgaga attaacattc    1740
cgtcaggaaa gcttggcttg gagcctgttg gtgcggtcat ggaattacct tcaacctcaa    1800
gccagaatgc agaatcactg cttttttgg ttgtgcttac ccatctctcc gcatcacctt    1860
tggtaaaggt tctaagctca ggtgagaaca tccctgcctg aacatgagaa aaaacagggg    1920
actcatactc acttctaagt gacggctgca tactaaccgc ttcatacatc tcgtagattt    1980
ctctggcgat tgaagggcta aattcttcaa cgctaacttt gagaattttt gcaagcaatg    2040
cggcgttata agcatttaat gcattgatgc cattaaataa agcaccaacg cctgactgcc    2100
ccatccccat cttgtctgcg acagattcct gggataagcc aagttcattt ttctttttt    2160 cataaattgc tttaaggcga cgtgcgtcct caagctgctc ttgtgttaat ggtttctttt    2220
ttgtgctcat acgttaaatc tatcaccgca agggataaat atctaacacc gtgcgtgttg    2280
actattttac ctctggcggt gataatggtt gcatgtacta aggaggttgt atggaacaac    2340
gcataaccct gaaagattat gcaatgcgct ttgggcaaac caagacagct aaagatct     2398
```

<210> SEQ ID NO 24
<211> LENGTH: 5557
<212> TYPE: DNA
<213> ORGANISM: Artificial Sequence
<220> FEATURE:
<223> OTHER INFORMATION: lambda fragment 22425-27972

<400> SEQUENCE: 24

```
ctgcagatct ggaaattgca acgaaggaag aaacctcgtt gctggaagcc tggaagaagt      60
atcgggtgtt gctgaaccgt gttgatacat caactgcacc tgatattgag tggcctgctg     120
tccctgttat ggagtaatcg ttttgtgata tgccgcagaa acgttgtatg aaataacgtt     180
ctgcggttag ttagtatatt gtaaagctga gtattggttt atttggcgat tattatcttc     240
aggagaataa tggaagttct atgactcaat tgttcatagt gtttacatca ccgccaattg     300
cttttaagac tgaacgcatg aaatatggtt tttcgtcatg ttttgagtct gctgttgata     360
tttctaaagt cggtttttt tcttcgtttt ctctaactat tttccatgaa atacattttt      420
gattattatt tgaatcaatt ccaattacct gaagtctttc atctataatt ggcattgtat     480
gtattggttt attggagtag atgcttgctt ttctgagcca tagctctgat atccaaatga     540
agccataggc atttgttatt ttggctctgt cagctgcata acgccaaaaa atatatttat     600
ctgcttgatc ttcaaatgtt gtattgatta aatcaattgg atggaattgt ttatcataaa     660
aaattaatgt ttgaatgtga taaccgtcct ttaaaaagt cgtttctgca agcttggctg      720
tatagtcaac taactcttct gtcgaagtga tattttagg cttatctacc agttttagac      780
gctctttaat atcttcagga attatttat tgtcatattg tatcatgcta aatgacaatt      840
tgcttatgga gtaatctttt aatttaaat aagttattct cctggcttca tcaaataaag     900
```

-continued

```
agtcgaatga tgttggcgaa atcacatcgt cacccattgg attgtttatt tgtatgccaa    960
gagagttaca gcagttatac attctgccat agattatagc taaggcatgt ataattcgt    1020
aatcttttag cgtattagcg acccatcgtc tttctgattt aataatagat gattcagtta   1080
aatatgaagg taatttcttt tgtgcaagtc tgactaactt ttttatacca atgtttaaca   1140
tactttcatt tgtaataaac tcaatgtcat tttcttcaat gtaagatgaa ataagagtag   1200
cctttgcctc gctatacatt tctaaatcgc cttgttttcc tatcgtattg cgagaatttt   1260
tagcccaagc cattaatgga tcattttttc attttcaat aacattattg ttataccaaa    1320
tgtcatatcc tataatctgg tttttgtttt tttgaataat aaatgttact gttcttgcgg   1380
tttggaggaa ttgattcaaa ttcaagcgaa ataattcagg gtcaaaatat gtatcaatgc   1440
agcatttgag caagtgcgat aaatctttaa gtcttctttc ccatggtttt ttagtcataa   1500
aactctccat tttgataggt tgcatgctag atgctgatat attttagagg tgataaaatt   1560
aactgcttaa ctgtcaatgt aatacaagtt gtttgatctt tgcaatgatt cttatcagaa   1620
accatatagt aaattagtta cacaggaaat ttttaatatt attattatca ttcattatgt   1680
attaaaatta gagttgtggc ttggctctgc taacacgttg ctcataggag atatggtaga   1740
gccgcagaca cgtcgtatgc aggaacgtgc tgcggctggc tggtgaactt ccgatagtgc   1800
gggtgttgaa tgatttccag ttgctaccga ttttacatat ttttgcatg agagaatttg    1860
taccacctcc caccgaccat ctatgactgt acgccactgt ccctaggact gctatgtgcc   1920
ggagcggaca ttacaaacgt ccttctcggt gcatgccact gttgccaatg acctgcctag   1980
gaattggtta gcaagttact accggattt gtaaaacag ccctcctcat ataaaagta     2040
ttcgttcact tccgataagc gtcgtaattt tctatctttc atcatattct agatccctct   2100
gaaaaaatct tccgagtttg ctaggcactg atacataact cttttccaat aattggggaa   2160
gtcattcaaa tctataatag gtttcagatt tgcttcaata aattctgact gtagctgctg   2220
aaacgttgcg gttgaactat atttccttat aacttttacg aaagagtttc tttgagtaat   2280
cacttcactc aagtgcttcc ctgcctccaa acgatacctg ttagcaatat ttaatagctt   2340
gaaatgatga agagctctgt gtttgtcttc ctgcctccag ttcgccgggc attcaacata   2400
aaaactgata gcacccggag ttccggaaac gaaatttgca tacccatt gctcacgaaa     2460
aaaaatgtcc ttgtcgatat agggatgaat cgcttggtgt acctcatcta ctgcgaaaac   2520
ttgacctttc tctcccatat tgcagtcgcg gcacgatgga actaaattaa taggcatcac   2580
cgaaaattca ggataatgtg caataggaag aaaatgatct atattttttg tctgtcctat   2640
atcaccacaa aatggacatt tttcacctga tgaaacaagc atgtcatcgt aatatgttct   2700
agcgggtttg tttttatctc ggagattatt ttcataaagc ttttctaatt taacctttgt   2760
caggttacca actactaagg ttgtaggctc aagagggtgt gtcctgtcgt aggtaaataa   2820
ctgacctgtc gagcttaata ttctatattg ttgttctttc tgcaaaaaag tggggaagtg   2880
agtaatgaaa ttatttctaa catttatctg catcatacct tccgagcatt tattaagcat   2940
ttcgctataa gttctcgctg gaagaggtag tttttcatt gtactttacc ttcatctctg    3000
ttcattatca tcgcttttaa aacggttcga ccttctaatc ctatctgacc attataattt   3060
tttagaatgg tttcataaga aagctctgaa tcaacggact gcgataataa gtggtggtat   3120
ccagaatttg tcacttcaag taaaacacc tcacgagtta aaacacctaa gttctcaccg    3180
aatgtctcaa tatccggacg gataatattt attgcttctc ttgaccgtag gactttccac   3240
atgcaggatt ttggaaccctc ttgcagtact actggggaat gagttgcaat tattgctaca  3300
```

```
ccattgcgtg catcgagtaa gtcgcttaat gttcgtaaaa aagcagagag caaaggtgga    3360
tgcagatgaa cctctggttc atcgaataaa actaatgact tttcgccaac gacatctact    3420
aatcttgtga tagtaaataa aacaattgca tgtccagagc tcattcgaag cagatatttc    3480
tggatattgt cataaaacaa tttagtgaat ttatcatcgt ccacttgaat ctgtggttca    3540
ttacgtctta actcttcata tttagaaatg aggctgatga gttccatatt tgaaaagttt    3600
tcatcactac ttagtttttt gatagcttca agccagagtt gtcttttttct atctactctc    3660
atacaaccaa taaatgctga aatgaattct aagcggagat cgcctagtga ttttaaacta    3720
ttgctggcag cattcttgag tccaatataa aagtattgtg taccttttgc tgggtcaggt    3780
tgttctttag gaggagtaaa aggatcaaat gcactaaacg aaactgaaac aagcgatcga    3840
aaatatccct ttgggattct tgactcgata agtctattat tttcagagaa aaaatattca    3900
ttgttttctg ggttggtgat tgcaccaatc attccattca aaattgttgt tttaccacac    3960
ccattccgcc cgataaaagc atgaatgttc gtgctgggca tagaattaac cgtcacctca    4020
aaaggtatag ttaaatcact gaatccggga gcactttttc tattaaatga aaagtggaaa    4080
tctgacaatt ctggcaaacc atttaacaca cgtgcgaact gtccatgaat ttctgaaaga    4140
gttacccctc taagtaatga ggtgttaagg acgctttcat tttcaatgtc ggctaatcga    4200
tttggccata ctactaaatc ctgaatagct ttaagaaggt tatgtttaaa accatcgctt    4260
aatttgctga gattaacata gtagtcaatg ctttcaccta aggaaaaaaa catttcaggg    4320
agttgactga attttttatc tattaatgaa aagtgcttta cttcttcttt ttgacctaca    4380
aaccaattt taacatttcc gatatcgcat ttttcaccat gctcatcaaa gacagtaaga    4440
taaaacattg taacaaagga atagtcattc caaccatctg ctcgtaggaa tgccttattt    4500
ttttctactg caggaatata cccgcctctt tcaataacac taaactccaa catatagtaa    4560
cccttaattt tattaaaata accgcaattt atttggcggc aacacaggat ctctctttta    4620
agttactctc tattacatac gttttccatc taaaaattag tagtattgaa cttaacgggg    4680
catcgtattg tagttttcca tatttagctt tctgcttcct tttggataac ccactgttat    4740
tcatgttgca tggtgcactg tttataccaa cgatatagtc tattaatgca tatatagtat    4800
cgccgaacga ttagctcttc aggcttctga agaagcgttt caagtactaa taagccgata    4860
gatagccacg gacttcgtag ccattttttca taagtgttaa cttccgctcc tcgctcataa    4920
cagacattca ctacagttat ggcggaaagg tatgcatgct gggtgtgggg aagtcgtgaa    4980
agaaaagaag tcagctgcgt cgtttgacat cactgctatc ttcttactgg ttatgcaggt    5040
cgtagtgggt ggcacacaaa gctttgcact ggattgcgag ctttgtgct tctctgga    5100
gcgacaggtt tgatgacaaa aaattagcgc aagaagacaa aaatcacctt gcgctaatgc    5160
tctgttacag gtcactaata ccatctaagt agttgattca tagtgactgc atatgttgtg    5220
ttttacagta ttatgtagtc tgttttttat gcaaatctca atttaatata ttgatattta    5280
tatcatttta cgtttctcgt tcagcttttt tatactaagt tggcattata aaaaagcatt    5340
gcttatcaat ttgttgcaac gaacaggtca ctatcagtca aaataaaatc attattttgat    5400
ttcaattttg tcccactccc tgcctctgtc atcacgatac tgtgatgcca tggtgtccga    5460
cttatgcccg agaagatgtt gagcaaactt atcgcttatc tgcttctcat agagtcttgc    5520
agacaaactg cgcaactcgt gaaaggtagg cggatcc                            5557
```

<210> SEQ ID NO 25
<211> LENGTH: 140

```
<212> TYPE: DNA
<213> ORGANISM: Artificial Sequence
<220> FEATURE:
<223> OTHER INFORMATION: combined synthetic polyA (SPA) sequence and a
      pausing signal from the human alpha2 globin gene

<400> SEQUENCE: 25
ataaaagatc cttattttca ctagttctgt gtgttggttt tttgtgtgaa catacgctct     60
ccatcaaaac aaaacgaaac aaaacaaact agcaaaatag gctgtcccca gtgcaagtgc    120
aggtgccaga acatttctct                                                140

<210> SEQ ID NO 26
<211> LENGTH: 870
<212> TYPE: DNA
<213> ORGANISM: Artificial Sequence
<220> FEATURE:
<223> OTHER INFORMATION: sequence of Inter histone H3FA-H4F

<400> SEQUENCE: 26
tatttgagga cactaacctg tgcgccatcc acgccaagcg cgtcactatc atgcccaagg     60
acatccagct cgcccgccgc atccgcggag agagggcgtg attactgtgg tctctctgac    120
ggtccaagca aaggctcttt tcagagccac cacctttca agtaaagtag ctgtaagaaa    180
ccaatttaag acaaaaggga atgcattggg agcactttc gttttaatgc tactgaaggc    240
ttcaaaacca atcgatttcg gccggtcgcg gtgactcacg cctgtaattc aagcactttg    300
agaggctgag gcgggcggat taccagaaat caggagttcg ggatcagcct ggccaacatg    360
gccgaatccc gtctctacga aaaatacaaa aacacgccgg gcgcgacggc gagcgcttgt    420
aatcccagct acactctgaa ggctgaggca ggagaaacac ttgaacctga gaggcagagg    480
tttcagtgaa tcgagatggc tctaatgtac tccagtctgg gcgacagaga gattcggtta    540 aaaaaaagt tcgacttaaa ataattctgg agtcagaatg ggtttacatt taattcttaa    600
cccagttcct caaagcctgt agctctgtta agaaaataaa ggccattggt caagcctgct    660
tggtcccacc ctcatctccc caccctcccc caatcgctgc tcccgccatt tcctggggct    720
tggaggaggg gttaaaggag cggactgtag gcgtcacatt tcccgcctgc gcgcttttca    780
gtctcagtgt ccgctggagg tggggcagg ggtaacgtag atatataaag atcggtttcc    840
tattctctca cttgctcttg gttcacttct                                    870

<210> SEQ ID NO 27
<211> LENGTH: 1173
<212> TYPE: DNA
<213> ORGANISM: Artificial Sequence
<220> FEATURE:
<223> OTHER INFORMATION: sequence of Inter histone H1F4-H2BFB

<400> SEQUENCE: 27
aaggcgccca agagcccagc gaaggccaaa gcagttaaac ccaaggcggc taaaccaaag     60
accgccaagc ccaaggcagc caagccaaag aaggcggcag ccaagaaaaa gtagaaagtt    120
cctttggcca actgcttaga agcccaacac aacccaaagg ctcttttcag agccaccac    180 cgctctcagt aaaagagctg ttgcactatt aggggcgtg gctcggaaa acgctgctaa    240 gcaggggcgg gtctcccggg aacaaagtcg gggagaggag tgggattttg tgtgtctccg    300
gagctatttt tgactaaggc gtcgcgtcgc ccaagccgga gtgcagtggc gtcatctcga    360
ttttgcgttc tcgagtgtcg gagttgaacc catttgggcc tcccttgtgc tttgcacttt    420
tagcaggccc tggcctccag atagcatggg aaaaaaaatg ttgggatttt cccgggtttc    480
```

| | |
|---|---|
| taagctgggt ttttccgagt tccaaacacg gcacagtgta tcagtttctg tgctggttac | 540 |
| aagcctactg gttatcccta tcgagtatgg caggcagtga gggacttcag aggagtacgt | 600 |
| cttaggacaa gtggcatagt actgacatta tttccgaagg gctacatttc aagtgcttgg | 660 |
| ggagactact gccacataac tgaaaattag aaaccgacac tgcagaaaaa tacttggtcc | 720 |
| ttaaatgtgg catttggatg gattaaggac ttgccgaaac gtaaaactga cagacttggg | 780 |
| ggggggggat gtcccaatta gcacggcttc tgtatgcaac gagtcccata ctttgttaaa | 840 |
| ggaagaaagg aatgtgagtt ctcctaatct gttaagtatc tttcggtgta agttctgaca | 900 |
| ccacaatgtt aaaaaagtcg atctcaaaa accaactgct ccaagcgaag tgcacagctg | 960 |
| tcttgcctaa agaggcctat ttatagtagc ctcgggtagt ctggtctggg ctttctcatt | 1020 |
| gggtacaagt aaaggaacga aatagccaat gaaaaggtag acttttaagt gtcgtttaca | 1080 |
| ttggcatttg tgacgacact ctaaaattaa tccaatcata aacgaaatct gattaacctc | 1140 |
| atttgaatac cgcatctata aatgaacagg gcc | 1173 |

```
<210> SEQ ID NO 28
<211> LENGTH: 1586
<212> TYPE: DNA
<213> ORGANISM: Artificial Sequence
<220> FEATURE:
<223> OTHER INFORMATION: sequence of STAR4

<400> SEQUENCE: 28
```

| | |
|---|---|
| gatctgagtc atgttttaag gggaggattc ttttggctgc tgagttgaga ttaggttgag | 60 |
| ggtagtgaag gtaaaggcag tgagaccacg taggggtcat tgcagtaatc caggctggag | 120 |
| atgatggtgg ttcagttgga atagcagtgc atgtgctgta acaacctcag ctgggaagca | 180 |
| gtatatgtgg cgttatgacc tcagctggaa cagcaatgca tgtggtggtg taatgacccc | 240 |
| agctgggtag ggtgcatgtg atggaacaac ctcagctggg tagcagtgta cttgataaaa | 300 |
| tgttggcata ctctagattt gttatgaggg tagtgccatt aaatttctcc acaaattggt | 360 |
| tgtcacgtat gagtgaaaag aggaagtgat ggaagacttc agtgcttttg gcctgaataa | 420 |
| atagaagacg tcatttccag ttaatggaga cagggaagac taaaggtagg gtgggattca | 480 |
| gtagagcagg tgttcagttt tgaatatgat gaactctgag agaggaaaaa cttttttctac | 540 |
| ctcttagttt ttgtgactgg acttaagaat taaagtgaca taagacagag taacaagaca | 600 |
| aaaatatgcg aggttattta atatttttac ttgcagaggg gaatcttcaa aagaaaaatg | 660 |
| aagacccaaa gaagccatta gggtcaaaag ctcatatgcc tttttaagta gaaaatgata | 720 |
| aattttaaca atgtgagaag acaaggtgt ttgagctgag ggcaataaat tgtgggacag | 780 |
| tgattaagaa atatatgggg gaaatgaaat gataagttat tttagtagat ttattcttca | 840 |
| tatctatttt ggcttcaact tccagtctct agtgataaga atgttcttct cttcctggta | 900 |
| cagagagagc acctttctca tgggaaattt tatgaccttg ctgtaagtag aaaggggaag | 960 |
| atctcctgtt tcccagcatc aggatgcaaa catttccctc cattccagtt ctcaaccca | 1020 |
| tggctgggcc tcatggcatt ccagcatcg tatgagtgca cctttcctgc aggctgcctc | 1080 |
| gggtagctgg tgcactgcta ggtcagtcta tgtgaccagg agctgggcct ctgggcaatg | 1140 |
| ccagttggca gcccccatcc ctccactgct ggggcctcc tatccagaag gcttggtgt | 1200 |
| gcagaacgat ggtgcaccat catcattccc cacttgccat ctttcagggg acagccagct | 1260 |
| gctttgggcg cggcaaaaaa cacccaactc actcctcttc aggggcctct ggtctgatgc | 1320 |
| caccacagga catccttgag tgctgggcag tctgaggaca gggaaggagt gatgaccaca | 1380 |

```
aaacaggaat ggcagcagca gtgacaggag gaagtcaaag gcttgtgtgt cctggccctg   1440
ctgagggctg gcgagggccc tgggatggcg ctcagtgcct ggtcggctgc aagaggccag   1500
ccctctgccc atgaggggag ctggcagtga ccaagctgca ctgccctggt ggtgcatttc   1560
ctgccccact ctttccttct aagatc                                       1586
```

<210> SEQ ID NO 29
<211> LENGTH: 1176
<212> TYPE: DNA
<213> ORGANISM: Artificial Sequence
<220> FEATURE:
<223> OTHER INFORMATION: sequence of STAR6

<400> SEQUENCE: 29

```
gatctgaccc accacagaca tcccctctgg cctcctgagt ggtttcttca gcacagcttc     60
cagagccaaa ttaaacgttc actctatgtc tatagacaaa aagggttttg actaaactct    120
gtgttttaga gagggagtta aatgctgtta acttttttagg ggtgggcgag aggaatgaca    180
aataacaact tgtctgaatg ttttacattt ctccccactg cctcaagaag gttcacaacg    240
aggtcatcca tgataaggag taagacctcc cagccggact gtccctcggc ccccagagga    300
cactccacag agatatgcta actggacttg gagactggct cacactccag agaaaagcat    360
ggagcacgag cgcacagagc agggccaagg tcccagggac agaatgtcta ggagggagat    420
tggggtgagg gtaatctgat gcaattactg tggcagctca acattcaagg gaggggaag     480 aaagaaacag tccctgtcaa gtaagttgtg cagcagagat ggtaagctcc aaaatttgaa    540
actttggctg ctggaaagtt ttaggggggca gagataagaa gacataagag actttgaggg    600
tttactacac actagacgct ctatgcattt atttatttat tatctcttat ttattacttt    660
gtataactct tataataatc ttatgaaaac ggaaaccctc atatacccat tttacagatg    720
agaaaagtga caattttgag agcatagcta agaatagcta gtaagtaaag gagctgggac    780
ctaaaccaaa ccctatctca ccagagtaca cactctttt ttattccagt gtaattttt      840 ttaatttta ttttactttta agttctggga tacatgtgca gaaggtatgg tttgttacat    900
aggtatatgt gtgccatagt ggattgctgc acctatcaac ccgtcatcta ggtttaagcc    960
ccacatgcat tagctatttg tcctgatgct ctccctcccc tccccacacc agacaggcct    1020
tggtgtgtga tgttccctc cctgtgtcca tgtgttctca ctgttcagct cccacttatg    1080
agtgagaaca tgtggtattt ggttttctgt tcctgtgtta gtttgctgag gatgatggct    1140
tccagcttca tccatgtccc tgcaaaggac acgatc                             1176
```

<210> SEQ ID NO 30
<211> LENGTH: 2094
<212> TYPE: DNA
<213> ORGANISM: Artificial Sequence
<220> FEATURE:
<223> OTHER INFORMATION: sequence of STAR7

<400> SEQUENCE: 30

```
gatcacccga ggtcaggagt tcaagaccag cctggccaac atggtaaaac ctcgtctcta     60
ctaaaaaaat acgaaaaatt agctggttgt ggtggtgcgt gcttgtaatc ccagctactc    120
gggaggctga ggcaggagaa tcacttgaat ctggggaggca gaggttgcag tgagctgaga    180
tagtgccatt gcactccagc ctgggcaaca gacggagact ctgtctccaa aaaaaaaaa     240 aaaaatctta gaggacaaga atggctctct caaacttttg aagaaagaat aaataaatta    300
tgcagttcta gaagaagtaa tggggatata ggtgcagctc atgatgagga agacttagct    360
```

```
taactttcat aatgcatctg tctggcctaa gacgtggtga gcttttatg tctgaaaaca    420 ttccaatata gaatgataat aataatcact tctgaccccc cttttttttc ctctccctag    480
actgtgaagc agaaacccca tattttctt agggaagtgg ctacgcactt tgtatttata    540
ttaacaacta ccttatcagg aaattcatat tgttgcccctt ttatggatgg ggaaactgga    600
caagtgacag agcaaaatcc aaacacagct ggggatttcc ctcttttaga tgatgatttt    660
aaaagaatgc tgccagagag attcttgcag tgttggagga catatatgac ctttaagata    720
ttttccagct cagagatgct atgaatgtat cctgagtgca tggatggacc tcagttttgc    780
agattctgta gcttatacaa tttggtggtt ttctttagaa gaaataaca catttataaa    840 tattaaaata ggcccaagac cttacaaggg cattcataca aatgagaggc tctgaagttt    900
gagtttgttc actttctagt taattatctc ctgcctgttt gtcataaatg cgtttagtag    960
ggagctgcta atgacaggtt cctccaacag agtgtggaag aaggagatga cggctggctt   1020
cccctctggg acagcctcag agctagtggg gaaactatgt tagcagagtg atgcagtgac   1080
caagaaaata gcactaggag aaagctggtc catgagcagc tggtgagaaa aggggtggta   1140
atcatgtatg cccttttcctg ttttattttt tattgggttt ccttttgcct ctcaattcct   1200
tctgacaata caaaatgttg gttggaacat ggagcacctg gaagtctggt tcatttttctc   1260 tcagtctctt gatgttctct cgggttcact gcctattgtt ctcagttcta cacttgagca   1320
atctcctcaa tagctaaagc ttccacaatg cagattttgt gatgacaaat tcagcatcac   1380
ccagcagaac ttaggttttt ttctgtcctc cgtttcctga cctttttctt ctgagtgctt   1440
tatgtcacct cgtgaaccat cctttcctta gtcatctacc tagcagtcct gattcttttg   1500
acttgtctcc ctacaccaca ataaatcact aattactatg gattcaatcc ctaaaatttg   1560
cacaaacttg caaatagatt acgggttgaa acttagagat ttcaaacttg agaaaaaagt   1620
ttaaatcaag aaaaatgacc tttaccttga gagtagaggc aatgtcattt ccaggaataa   1680
ttataataat attgtgttta atatttgtat gtaacatttg aataccttca atgttcttat   1740
ttgtgttatt ttaatctctt gatgttacta actcatttgg tagggaagaa aacatgctaa   1800
aataggcatg agtgtcttat taaatgtgac aagtgaatag atggcagaag gtggattcat   1860
attcagtttt ccatcaccct ggaaatcatg cggagatgat ttctgcttgc aaataaaact   1920
aacccaatga ggggaacagc tgttcttagg tgaaaacaaa acaaacacgc caaaaacctt   1980
tattctcttt attatgaatc aaattttttcc tctcagataa ttgttttatt tatttatttt   2040
tattattatt gttattatgt ccagtctcac tctgtcgcct aagctggcat gatc         2094
```

<210> SEQ ID NO 31
<211> LENGTH: 1031
<212> TYPE: DNA
<213> ORGANISM: Artificial Sequence
<220> FEATURE:
<223> OTHER INFORMATION: sequence of STAR12

<400> SEQUENCE: 31

```
atcctgcttc tgggaagaga gtggcctccc ttgtgcaggt gactttggca ggaccagcag     60
aaacccaggt ttcctgtcag gaggaagtgc tcagcttatc tctgtgaagg gtcgtgataa    120
ggcacgagga ggcaggggct tgccaggatg ttgccttttct gtgccatatg gacatctca    180 gcttacgttg ttaagaaata tttggcaaga agatgcacac agaatttctg taacgaatag    240
gatggagttt taagggttac tacgaaaaaa agaaaactac tggagaagag ggaagccaaa    300
caccaccaag tttgaaatcg attttattgg acgaatgtct cactttaaat ttaaatggag    360
```

-continued

```
tccaacttcc ttttctcacc cagacgtcga gaaggtggca ttcaaaatgt ttacacttgt      420
ttcatctgcc tttttgctaa gtcctggtcc cctacctcct ttccctcact tcacatttgt      480
cgtttcatcg cacacatatg ctcatcttta tatttacata tatataattt ttatatatgg      540
cttgtgaaat atgccagacg agggatgaaa tagtcctgaa aacagctgga aaattatgca      600
acagtgggga gattgggcac atgtacattc tgtactgcaa agttgcacaa cagaccaagt      660
ttgttataag tgaggctggg tggttttat tttttctcta ggacaacagc ttgcctggtg       720
gagtaggcct cctgcagaag gcatttctt aggagcctca acttccccaa gaagaggaga      780
gggcgagact ggagttgtgc tggcagcaca gagacaaggg ggcacggcag gactgcagcc      840
tgcagagggg ctggagaagc ggaggctggc acccagtggc cagcgaggcc caggtccaag      900
tccagcgagg tcgaggtcta gagtacagca aggccaaggt ccaaggtcag tgagtctaag      960
gtccatggtc agtgaggctg agacccaggg tccaatgagg ccaaggtcca gagtccagta     1020
aggccgagat c                                                          1031
```

<210> SEQ ID NO 32
<211> LENGTH: 995
<212> TYPE: DNA
<213> ORGANISM: Artificial Sequence
<220> FEATURE:
<223> OTHER INFORMATION: sequence of STAR18

<400> SEQUENCE: 32

```
ctaaaggcat tttatataga gctgtggttt ttgtggttta cctgtggccg tggccagagg       60
ttcctgggag gctaacaggt gttttttgag ggttggggct tgggtgggg tggggtgaat      120 tctctgtttc taggatgtgc ttggtgtttg aatctaggct ttagtgactg atgctggtta     180
atttctaggg ttgatggttt attgggcctt gtgttgtatg agatggaatt ttaaatattt     240
ttaaatgttt ctctagttct tagagaaatt tttaagcaac tcaagatagg ctcttcccgc     300
atatgataat ccgtcaggtg aatttggatt cttttatatc acaaaatgaa tccatgtttt     360
gggaggtaat ggtatcagaa tatatggtgc aggtcttggt aaaaacccaa tagatctttg     420
agaaatacaa gacatctctg tgttgaaaca tcgtgtgttt cttatttgcc agagtaggaa     480
aagagtagat cttttttgctc tctaaatgta ttgatgggtt gtgttttttt tcccacctgc    540
taataaatat tacattgcaa cattcttccc tcaacttcaa aactgctgaa ctgaaacaat     600
atgcataaaa gaaatccctt tgcagaagaa aaaagctat tttctcccac tgattttgaa      660
tggcacttgc ggatgcagtt cgcaaatcct attgcctatt ccctcatgaa cattgtgaaa     720
tgaaaccttt ggacagtctg ccgcattgcg catgagactg cctgcgcaag gcaagggtat    780
ggttcccaaa gcacccagtg gtaaatccta acttattatt cccttaaaat tccaatgtaa    840
caacgtgggc cataaaagag tttctgaaca aaacatgtca ctttgtggaa aggtgttttt    900
cgtaattaat gatggaatca tgctcatttc aaaatggagg tccacgattt gtggccagct    960
gatgcctgca aattatcctg atcactaac tctga                                 995
```

<210> SEQ ID NO 33
<211> LENGTH: 891
<212> TYPE: DNA
<213> ORGANISM: Artificial Sequence
<220> FEATURE:
<223> OTHER INFORMATION: sequence of STAR35

<400> SEQUENCE: 33

```
cgacttggtg atgcgggctc tttttggtt ccatatgaac tttaaagtag tcttttccaa       60
```

```
ttctgtgaag aaagtcattg gtaggttgat ggggatggca ttgaatctgt aaattacctt      120
gggcagtatg gccattttca caatgttgat tcttcctatc catgatgatg gaatgttctt      180
ccattagttt gtatcctctt ttatttcctt gagcagtggt ttgtagttct ccttgaagag      240
gtccttcaca tcccttgtaa gttggattcc taggtatttt attctctttg aagcaattgt      300
gaatgggagt tcactcacga tttggctctc tgtttgtctg ctggtgtata agaatgtttg      360
tgattttgt acattgattt tgtatcctga gactttgctg aagttgctta tcagcttaag       420
gagcttttgg gctgagacaa tgggattttc tagatataca atcatgtcgt ctgcaaacag      480
ggacaatttg acttcctctt ttcctaattg aatacacttt atctccttct cctgcctaat      540
tgccctgggc agaacttcca acactatgtt gaataggagt ggtgagagag gcatccctg       600
tcttgtgcca gttttcaaag ggaatgcttc cagtttttgc ccattcagta tgatattggc      660
tgtgggtttg tcatagatag ctcttattat tttgaaatgt gtcccatcaa tacctaattt      720
attgagagtt tttagcatga agcattgttg aattttgtca aaggcttttt ctgcatctat      780
tgagataatc atgtggtttt tgtctttggc tctgtttata tgctggatta catttattga      840
tttgtgtata ttgaaccagc cttgcatccc agggatgaag cccacttgat c               891
```

<210> SEQ ID NO 34
<211> LENGTH: 1031
<212> TYPE: DNA
<213> ORGANISM: Artificial Sequence
<220> FEATURE:
<223> OTHER INFORMATION: sequence of STAR40

<400> SEQUENCE: 34

```
gatcaagaaa gcactccggg ctccagaagg agccttccag gccagctttg agcataagct       60
gctgatgagc agtgagtgtc ttgagtagtg ttcagggcag catgttacca ttcatgcttg      120
acttctagcc agtgtgacga gaggctggag tcaggtctct agagagttga gcagctccag      180
ccttagatct cccagtctta tgcggtgtgc ccattcgctt tgtgtctgca gtccctggc       240
cacacccagt aacagttctg ggatctatgg gagtagcttc cttagtgagc tttcccttca      300
aatactttgc aaccaggtag agaagtttgg agtgaaggtt ttgttcttcg tttcttcaca      360
atatggatat gcatcttctt ttgaaaatgt taaagtaaat tacctctctt ttcagatact      420
gtcttcatgc gaacttggta tcctgtttcc atcccagcct tctataaccc agtaacatct      480
tttttgaaac cagtgggtga gaaagacacc tggtcaggaa cgcggaccac aggacaactc      540
aggctcaccc acggcatcag actaaaggca aacaaggact ctgtataaag taccggtggc      600
atgtgtatta gtggagatgc agcctgtgct ctgcagacag ggagtcacac agacactttt      660
ctataatttc ttaagtgctt tgaatgttca agtagaaagt ctaacattaa atttgattga      720
acaattgtat attcatggaa tattttggaa cggaatacca aaaatggca atagtggttc       780
tttctggatg gaagacaaac ttttcttctt taaaataaat tttattttat atatttgagg      840
ttgaccacat gacctaagg atacatatag acagtaaact ggttactaca gtgaagcaaa       900
ttaacatatc taccatcgta catagttaca tttttttgtg tgacaggaac agctaaaatc      960
tacgtattta acaaaactcc taaagacaat acatttttat taactatagc cctcatgatg     1020
tacattagat c                                                          1031
```

METHOD FOR IMPROVING PROTEIN PRODUCTION

CROSS-REFERENCE TO RELATED APPLICATIONS

This application is a continuation of U.S. patent application Ser. No. 11/157,193, filed Jun. 20, 2005, now U.S. Pat. No. 7,413,896 (Aug. 19, 2008), which application is a continuation of PCT International Patent Application No. PCT/NL2003/000850, filed on Dec. 2, 2003, designating the United States of America, and published in English, as PCT International Publication No. WO 2004/055215 A1 on Jul. 1, 2004, which application claims priority to European Patent Application No. 02080347.4 filed Dec. 18, 2002, the entirety of each of which being incorporated herein by this reference.

TECHNICAL FIELD

The invention relates to the fields of biotechnology, biochemistry, molecular biology, and pharmacology. More specifically, the present invention relates to the production of proteins in a (host) cell.

BACKGROUND

Proteins are produced in systems for a wide range of applications in biology and biotechnology. These include research into cellular and molecular function, production of proteins as biopharmaceuticals or diagnostic reagents, and modification of the traits or phenotypes of livestock and crops. Biopharmaceuticals are usually proteins that have an extracellular function, such as antibodies for immunotherapy or hormones or cytokines for eliciting a cellular response. Proteins with extracellular functions exit the cell via the secretory pathway and undergo post-translational modifications during secretion (Chevet et al. 2001). The modifications (primarily glycosylation and disulfide bond formation) do not occur in bacteria. Moreover, the specific oligosaccharides attached to proteins by glycosylating enzymes are species and cell-type specific. These considerations often limit the choice of host cells for heterologous protein production to eukaryotic cells (Kaufman 2000). For expression of human therapeutic proteins, host cells such as bacteria, yeast, or plants may be inappropriate. Even the subtle differences in protein glycosylation between rodents and human, for example, can be sufficient to render proteins produced in rodent cells unacceptable for therapeutic use (Sheeley et al. 1997). The consequences of improper (i.e., non-human) glycosylation include immunogenicity, reduced functional half-life, and loss of activity. This further limits the choice of host cells to human cell lines or to cell lines such as Chinese Hamster Ovary (CHO) cells, which may produce glycoproteins with human-like carbohydrate structures (Liu 1992).

Some proteins of biotechnological interest are functional as multimers, i.e., they consist of two or more possibly different polypeptide chains in their biologically and/or biotechnologically active form, for example, antibodies (Wright and Morrison 1997). Production of such multimeric proteins in heterologous systems is technically difficult due to a number of limitations of current expression systems. These limitations include (1) difficulties in isolating recombinant cells/cell lines that produce the monomer polypeptides at high levels (predictability and yield), and (2) declines in the levels of expression during the industrial production cycle of the proteins (stability). These problems are described in more detail below.

(1) Recombinant proteins such as antibodies that are used as therapeutic compounds need to be produced in large quantities. The host cells used for recombinant protein production must be compatible with the scale of the industrial processes that are employed. Specifically, the transgene (or the gene encoding a protein of interest; the two terms are used interchangeably herein) expression system used for the heterologous protein needs to be retained by the host cells in a stable and active form during the growth phases of scale-up and production. This is achieved by integration of the transgene into the genome of the host cell. However, creation of recombinant cell lines by conventional means is a costly and inefficient process due to the unpredictability of transgene expression among the recombinant host cells. The unpredictability stems from the high likelihood that the transgene will become inactive due to gene silencing (McBurney et al. 2002). Using conventional technologies, the proportion of recombinant host cells that produce one polypeptide at high levels ranges from 1 to 2%. In order to construct a cell line that produces two polypeptides at high levels, the two transgenes are generally integrated independently. If the two transgenes are transfected simultaneously on two separate nucleic acids, the proportion of cells that will produce both polypeptides at high levels will be the arithmetic product of the proportions for single transgenes. Therefore, the proportion of such recombinant cell lines ranges from one in 2,500 to one in 10,000. For multimeric proteins with three or more subunits, the proportions decline further. These high-producing cell lines must subsequently be identified and isolated from the rest of the population. The methods required to screen for these rare high-expressing cell lines are time-consuming and expensive.

An alternative to simultaneous transfection of two transgene-bearing nucleic acids is sequential transfection. In this case the proportion of high-yielding clones will be the sum of the proportions for single transgenes, i.e., 2 to 4%. Sequential transfection however has (major) drawbacks, including high costs and poor stability. The high costs results from various factors: in particular, the time and resources required for screening for high-expressing cell lines is doubled, since high expression of each subunit must be screened for separately. The poor overall stability of host cells expressing two polypeptides is a consequence of the inherent instability of each of the two transgenes.

(2) Silencing of transgene expression during prolonged host cell cultivation is a commonly observed phenomenon. In vertebrate cells, it can be caused by formation of heterochromatin at the transgene locus, which prevents transcription of the transgene. Transgene silencing is stochastic; it can occur shortly after integration of the transgene into the genome or only after a number of cell divisions. This results in heterogeneous cell populations after prolonged cultivation, in which some cells continue to express high levels of recombinant protein while others express low or undetectable levels of the protein (Martin and Whitelaw 1996, McBurney et al. 2002). A cell line that is used for heterologous protein production is derived from a single cell, yet is often scaled up to, and maintained for long periods at, cell densities in excess of ten million cells per milliliter in cultivators of 1,000 liters or more. These large cell populations ($10^{14}$ to $10^{16}$ cells) are prone to serious declines in productivity due to transgene silencing (Migliaccio et al. 2000, Strutzenberger et al. 1999).

The instability of expression of recombinant host cells is particularly severe when transgene copy numbers are amplified in an attempt to increase yields. Transgene amplification is, for example, achieved by including a selectable marker gene such as dihydrofolate reductase (DHFR) with the transgene during integration (Kaufman 2000). Increased concentrations of the selection agent (in the case of DHFR, the drug methotrexate) select for cells that have amplified the number of DHFR genes in the chromosome (Kaufman and Sharp 1982). Since the transgene and DHFR are co-localized in the chromosome, the transgene copy number increases too. This is correlated with an increase in the yield of the heterologous protein (Kaufman 1990). However, the tandem repeats of transgenes that result from amplification are highly susceptible to silencing (Garrick et al. 1998, Kaufman 1990, McBurney et al. 2002).

A need exists for an alternative (heterologous) protein expression technology and specifically a protein expression method that overcomes the above outlined problems. Even more needed is an expression system that i) provides high predictability of expression, allowing balanced expression of multiple chains, ii) provides high yields and, iii) provides stability during an extended period during which the protein needs to be produced in large quantities. This stability is particularly needed when high copy numbers are present in a cell and silencing is likely to occur.

DISCLOSURE OF THE INVENTION

In one embodiment, the present invention uses a TRAnscription Pause ("TRAP") sequence to enhance a protein expression characteristic of a protein expression unit. It is thought that a TRAP at least in part prevents formation of antisense RNA or to prevent, at least in part, transcription to enter the protein expression unit. Without being bound by theory, it is believed that the present counter-intuitive blocking of transcription leads to stable transcription of a transgene. Due to the blocking, no antisense RNA is formed and hence the formation of (double-strand) dsRNA is inhibited. This could lead to a reduction or complete prevention of so-called RNAi, which involves the formation of dsRNAs of 21 to 23 base pairs. RNAi is thought to be involved in gene silencing. One way of function of the present invention could be that such RNAi-induced silencing is, at least in part, prevented.

How can dsRNA be produced from transgenes that are not designed to do so? The situation is easiest to imagine when transgenes integrate as multiple copies in inverted orientations into the genome and when, as a result, the transcription of the transgenes is convergent (FIG. 1A). In this case, transcription starting at one transgene continues into the next, resulting in an RNA that is self-complementary (sense and anti-sense). The formation of dsRNA can also occur with multiple copies of nucleic acid that harbor two transgene expression units, gene 1 and gene 2, which are oriented divergent (FIG. 1B). In this example, both sense mRNA and anti-sense RNA of gene 2 can be formed: sense gene 2 mRNA by the promoter on the left nucleic acid that drives gene 2, anti-sense gene 2 RNA by the promoter on the right nucleic acid that drives gene 1. Also, both sense mRNA and anti-sense RNA of gene 1 can be formed: sense gene 1 mRNA by the promoter on the right nucleic acid that drives gene 1, anti-sense gene 1 RNA by the promoter on the left nucleic acid that drives gene 2.

Even when one transgene on one nucleic acid integrates as single copy, dsRNA can be formed when transcription starts from an endogenous promoter that is located outside the transgene. This can easily happen if by chance the single copy integrates in a genomic location with an endogenous promoter present in such an orientation that anti-sense RNA is produced (FIG. 1C) (Stam et al. 2000). dsRNA formation is, however, most likely when multiple copies of the transgene are integrated as inverted repeats, because the complementary strands will always be connected. This is particularly relevant since, in most cases, a transgene will integrate with multiple copies. It is common practice that at the 3' end of a gene, a SV40 transcriptional terminator is placed. However, even the presence of such a polyadenylation signal downstream from the upstream expression unit is insufficient to prevent read-through transcription in the second downstream transcription unit (Eszterhas et al. 2002).

Usually, DNA sequences such as the SV40 polyadenylation signal are used to terminate transcription by placing the SV40 polyadenylation signal immediately downstream of a gene that is expressed (FIGS. 2A-2C). In other words, transcription should be prevented from continuing downstream of the gene. In the present invention, transcription blockers (TRAP) are preferably placed both upstream and downstream of the entire expression units, in such a manner that they prevent transcription to enter the expression units, this coming from upstream or downstream of the expression units (FIGS. 2A-2C). The orientation of TRAP when placed downstream is opposite of the usual orientation of the SV40 polyadenylation signals that are placed downstream of genes (FIGS. 2A-2C).

In one embodiment, the invention provides a method for expression (or producing) of at least one protein of interest in a cell comprising providing the cell with at least one protein expression unit that comprises a promoter functionally linked to an open reading frame encoding at least one protein of interest, characterized in that the protein expression unit further comprises at least one TRAP sequence and wherein the TRAP sequence is functionally located downstream of the open reading frame and at least in part prevents formation of antisense RNA. Preferably, at least one TRAP sequence is in a 3'-5' orientation (in relation to the coding region).

Preferably, the TRAP sequence reduces the formation of antisense RNA to a non-detectable level. Due to the presence of the TRAP, the formation of antisense RNA is, at least in part, prevented and hence the amount of dsRNA is decreased. As a consequence, the level of small dsRNAs of 21 to 23 base pairs (RNAi) is also decreased and the corresponding (full-length) RNA encoding a protein of interest will not be degraded. Hence, translation of the corresponding RNA results in (increased) expression of a protein of interest.

Surprisingly, as disclosed herein with the experimental part (Example 5), the use of TRAP sequences improves stability of expression.

In the above-outlined embodiment, the TRAP sequence can, for example, be a terminator and/or a polyadenylation signal sequence but in an orientation that differs from a possibly used terminator sequence behind an open reading frame in the protein expression unit (see, for example, FIG. 2A). However, it is entirely possible that there are TRAP sequences that are bi-directional. Thus, in the above embodiment, it is only necessary that the TRAP comprises a TRAP function in the reverse orientation. In another embodiment, the invention provides a method for expression (or producing) of at least one protein of interest in a cell comprising providing the cell with at least one protein expression unit that comprises a promoter functionally linked to an open reading frame encoding at least one protein of interest, characterized in that the protein expression unit further comprises at least one TRAP sequence and wherein the TRAP sequence is located upstream of the promoter and at least in part prevents transcription to enter the protein expression unit. Preferably, at least one TRAP sequence is in a 5'-3' orientation (in relation to the coding region).

Again, a TRAP sequence used in the latter embodiment can be a terminator and/or a polyadenylation signal sequence but this time, the TRAP sequence is in an unusual position with regard to the open reading frame because the TRAP is located upstream of the promoter that drives expression of the open reading frame.

In this embodiment, the presence of a TRAP sequence at least in part prevents transcription from a promoter sequence located outside a protein expression unit. Hence, the RNA from the protein expression unit does not have to compete with other RNA and hence a more efficient protein production system is provided.

The use of a TRAP to prevent, at least in part, formation of antisense RNA or to prevent, at least in part, transcription to enter the protein expression unit, isolates the protein expression unit from negative effects, like formation of RNAi, from outside the unit.

Nucleic acid integration in the genome of a cell occurs frequently in so-called concatemers. A concatemer of two integrated nucleic acids can have one of two organizations, either the two nucleic acids form a direct repeat or an inverted repeat. Concatemers having three or more integrated copies can have any combination of the two basic forms, together with occasional alterations such as deletions/mutations, etc. Typically, the integrated copies have their own transcription termination signals or analogous signals. The presence thereof typically results in a reduction of the amount of transcription that proceeds into the flanking integrated nucleic acid.

In embodiments of the invention that are also referred to herein, any residual transcription is prevented, at least in part, from entering the protein expression unit present in the co-integrated nucleic acid by means of a TRAP sequence that is also present on the co-integrated nucleic acid. In another embodiment, this residual transcription is prevented, at least in part, from entering into the co-integrated nucleic acid by the presence of a TRAP sequence within the integrated nucleic acid itself, i.e., thereby preventing transcription from entering the co-integrated nucleic acid. In this particular embodiment, a protein expression unit comprises a TRAP sequence downstream from the protein expression unit and in a 5'-3' orientation with respect to the protein expression unit, in addition to the usual signal(s) to terminate transcription of the protein expression unit. In a preferred version of this particular embodiment, the protein expression unit comprises two consecutive TRAP sequences in the same orientation, wherein both of the TRAP sequences are located downstream from the gene of interest and, at least in part, prevent transcription from entering the transcription unit of a co-integrated unit in a concatemer.

DESCRIPTION OF THE FIGURES

FIG. 1 is a schematic diagram of the invention.

FIG. 1A shows a single expression unit gene 1 under the control of the CMV promoter on one plasmid. This plasmid has integrated as multiple copies into the genome in such an orientation that the transcription is convergent. Consequently, there will be read-through transcription from copy one into copy two and vice versa. This will result in the formation of dsRNA. This plasmid suffers from silencing of the genes.

FIG. 1B shows two expression units, gene 1 and gene 2, both under the control of the CMV promoter and located in a divergent orientation on one plasmid. This plasmid has integrated as multiple copies into the genome. No matter what the orientation, there will always be read-through transcription from one gene on copy one into another gene on copy two. This results in the formation of dsRNA. This plasmid suffers from silencing of the genes.

FIG. 1C shows a single expression unit gene 1 under the control of the CMV promoter on one plasmid. This plasmid has integrated as a single copy into the genome. When integration is adjacent of a promoter that is oriented in a convergent manner relative to the plasmid, there will be read-through transcription from that promoter into gene 1 of the plasmid. This will result in the formation of dsRNA. This plasmid suffers from silencing of the genes.

FIG. 2A shows the first expression unit. It is flanked by TRAPs and STAR elements, and comprises a bicistronic gene containing (from 5' to 3') a transgene (encoding, for example, a reporter gene or one subunit of a multimeric protein; Gene), an IRES, and a selectable marker (zeo, conferring zeocin resistance) under control of the CMV promoter. A monocistronic selectable marker (puro) under control of the SV40 promoter is included. Both genes have the SV40 transcriptional terminator at their 3' ends (t). The TRAPs are drawn as an arrow indicating that in this particular orientation, transcription driven by any promoter outside the expression unit does not enter the expression unit.

FIG. 2B shows two expression units on one plasmid. Both Gene 1 and Gene 2 are both part of a bicistronic gene containing (from 5' to 3') a transgene (Gene 1), an IRES, and a selectable marker (zeo with Gene 1 and puro with Gene 2) under control of the CMV promoter and the SV40 transcriptional terminator (t). The entire cassette is surrounded by STAR elements and TRAPs; the latter are oriented in such a manner that transcription is kept out of the cassette and STAR elements.

FIG. 2C shows one expression unit. It is flanked by TRAPs and STAR elements and comprises a bicistronic gene containing (from 5' to 3') a transgene (encoding, for example, a reporter gene or one subunit of a multimeric protein; Gene), an IRES, and a selectable marker (zeo, conferring zeocin resistance) under control of the CMV promoter. The gene has the SV40 transcriptional terminator at their 3' ends (t). One TRAP sequence is placed upstream of the STAR that is adjacent to the CMV promoter. Two TRAPs are placed to flank the 3' STAR. The upstream TRAP sequence (5'-3') is oriented to prevent transcription to leak out of the CMV-driven expression unit. The downstream TRAP sequence (3'-5') is oriented to prevent transcription driven by any promoter outside the expression unit to enter the expression unit.

Figure 2:
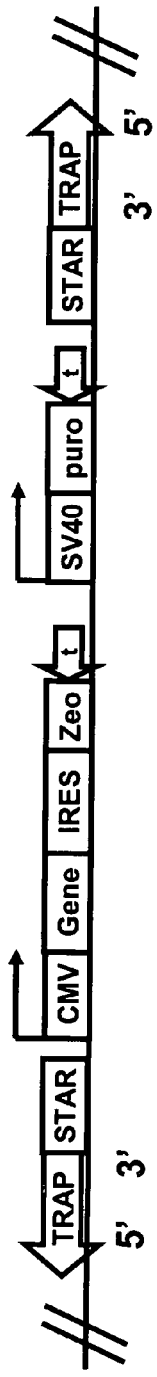
FIG. 2 is a schematic diagram of the invention.
Figure 2:
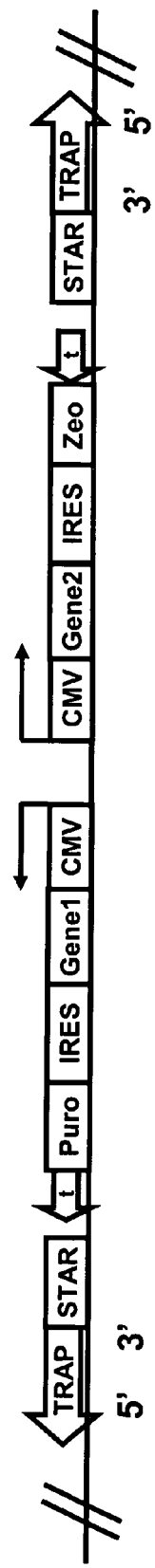
Figure 2:
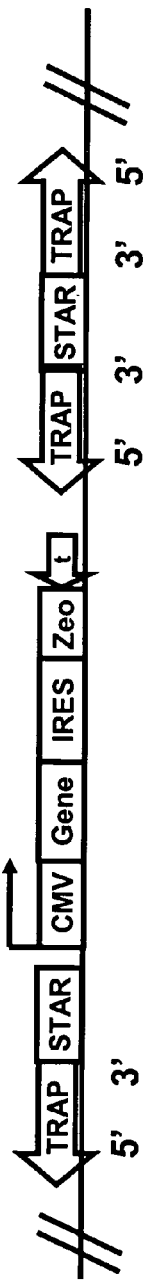

After the transfection selection by hygromycin, mRNA is isolated and blotted. The blot is incubated with a radioactive-labeled probe encompassing the codA gene. As a loading control, the blot is also incubated with a radioactive probe encompassing the hygromycin-resistance gene. The lambda (bp 35711-38103) fragment efficiently blocks transcription of the codA gene driven by the CMV promoter in the 5'-3' orientation (lane 2), but not in the 3'-5' orientation (lane 3). Also, a synthetic polyA (SPA) sequence, either alone (lane 8) or in combination with a 92 bp long a globin-pausing signal (lane 9), efficiently block transcription in the 5'-3' orientation, but not in the 3'-5' orientation (lanes 10 and 11). Neither MAZ sequence (lane 4), STAR7 (lane 5) nor STAR40 (lane 6) prevent transcription of the codA gene driven by the CMV promoter. All signals are compared to the control vector that contains no putative TRAP sequence (lanes 1 and 7).

Figure 5:
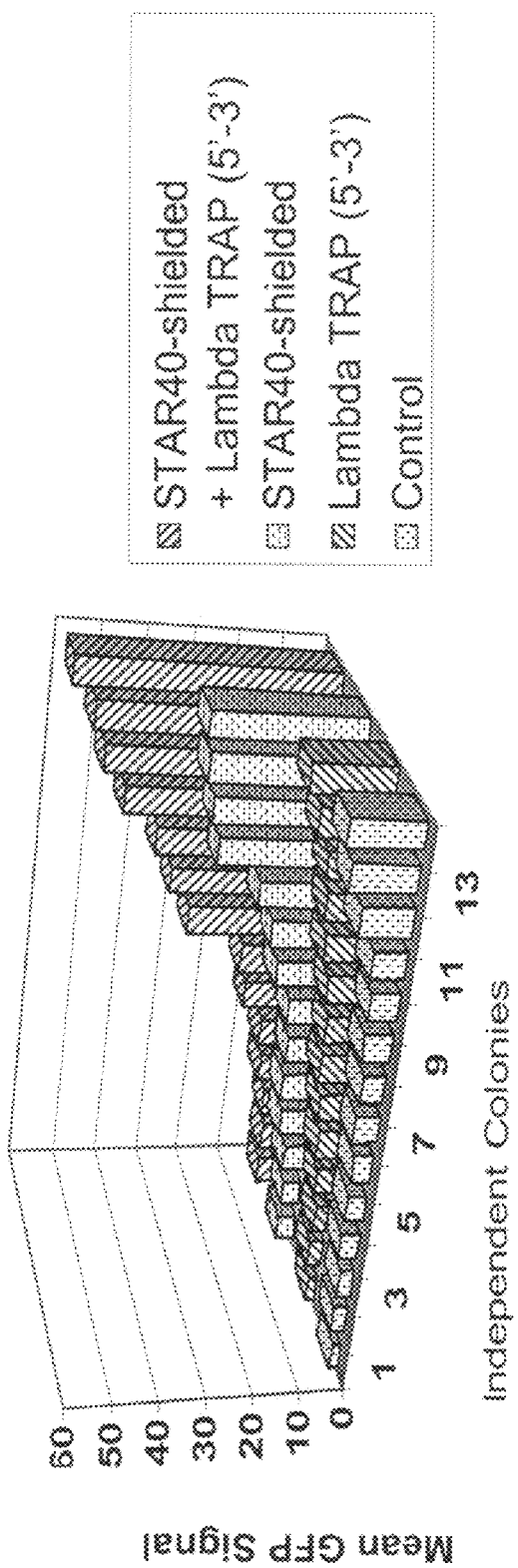

FIG. 5 illustrates TRAPs improve the effects of STAR elements on transgene expression. Constructs that are flanked with the lambda (bp 35711-38103) TRAP in the A orientation, STAR40 or the combined lambda (bp 35711-38103) TRAP/STAR40 are transfected to CHO-K1 cells. The 5'-3' orientation of the lambda (bp 35711-38103) TRAP results in transcription blocking (FIG. 3) and the TRAPs are placed to flank to entire constructs such that transcription cannot enter the expression units. Stable colonies (14 of each construct) are expanded and the GFP signal is determined on a XL-MCL Beckman Coulter flow cytometer. For each independent colony, the mean of the GFP signal is plotted. This is taken as a measure for the level of GFP expression. The results are compared to colonies that are transfected with a construct containing neither lambda (bp 35711-38103) TRAP nor STAR element (Control).

Figure 3:
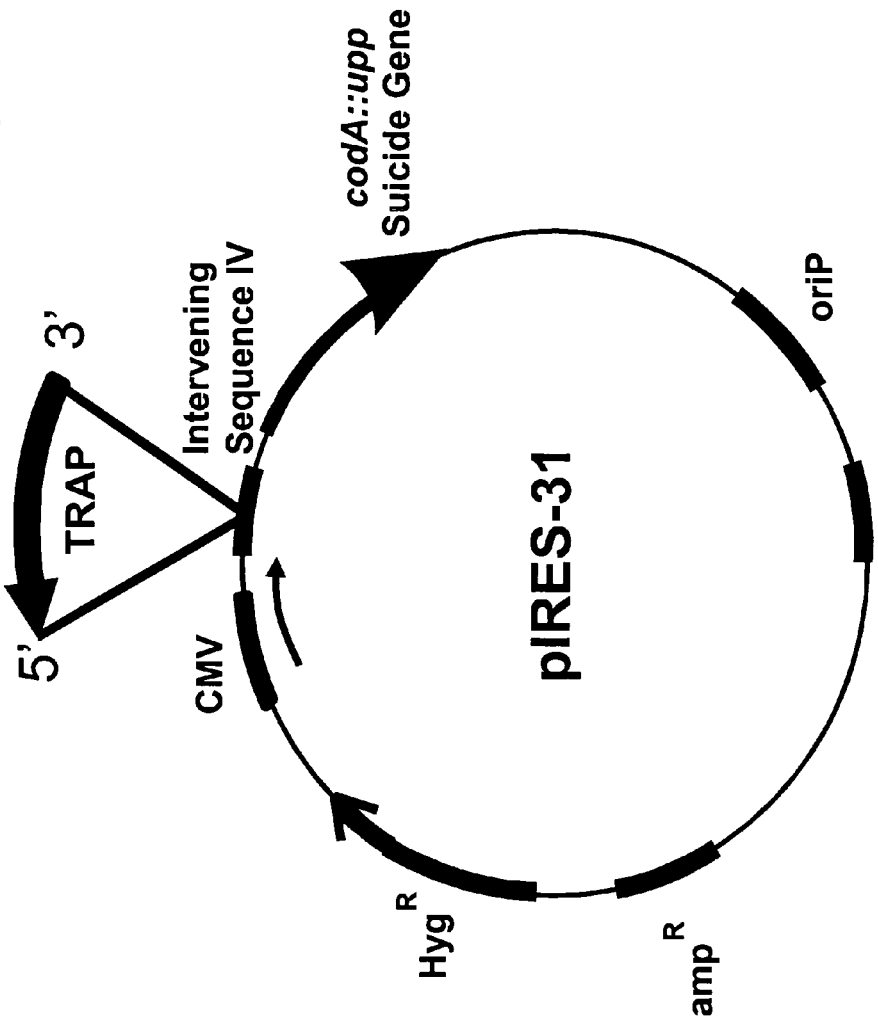
FIG. 3. The pcodA plasmid to identify and test putative TRAPs. The pIRES-31 plasmid contains the CMV promoter upstream of an Intervening Sequence IV (Clontech) that contains a multiple cloning site in which putative TRAPs are cloned. Downstream is the codA::upp suicide gene. The plasmid further comprises the hygromycin-resistance gene that is under control of the SV40 promoter. The plasmid also has an origin of replication (ori) and ampicillin-resistance gene (amp$^R$) for propagation in *Escherichia coli* and the EBNA-1 nuclear antigen for high copy episomal replication. The TRAP is drawn as an arrow indicating that the TRAP blocks transcription driven by the CMV promoter in this particular orientation. This is of importance for the orientation of TRAPs in FIG. 2, which are also drawn as arrows to indicate the specific orientation of the TRAPs to prevent transcription driven by any promoter outside the expression unit to enter this expression unit.
Figure 6:
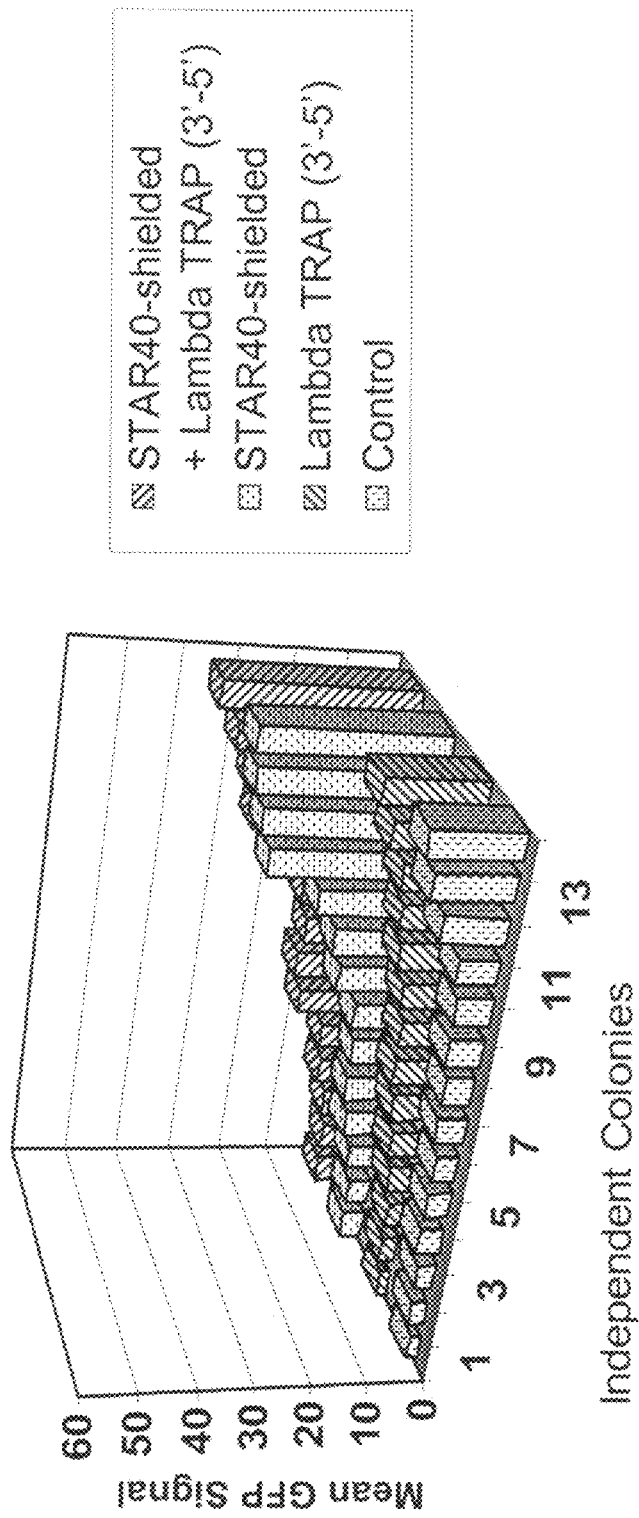

FIG. 6 shows TRAPs act in an orientation-dependent manner. Constructs that are flanked with the lambda (bp 35711-38103) TRAP in the 3'-5' orientation, STAR40 or the combined lambda (bp 35711-38103) TRAP/STAR40 are transfected to CHO-K1 cells. The 3'-5' orientation of the lambda (bp 35711-38103) TRAP does not result in transcription blocking (FIG. 3). Analysis of stable colonies is as in FIG. 5.

Figure 7:
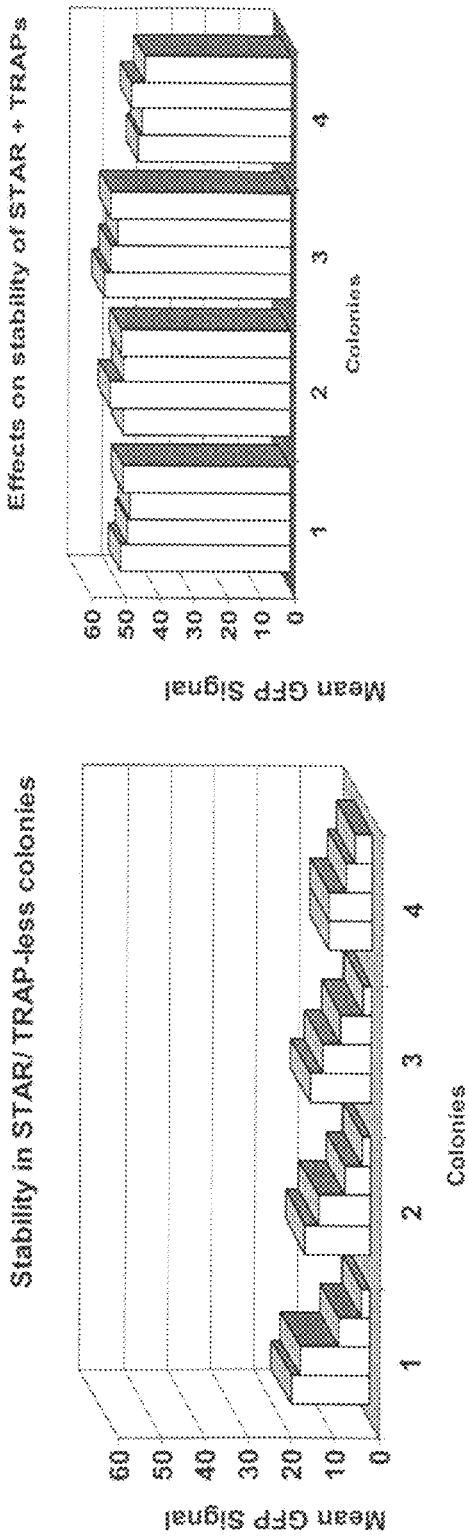

FIG. 7 illustrates TRAPs and STARs improve the stability of transgene expression. Stably transfected colonies that contain either a lambda (bp 35711-38103) TRAP/STAR-less (Control) GFP construct or the GFP construct that is flanked by the combined lambda (bp 35711-38103) TRAP/STAR40 are expanded. From both categories, four colonies are chosen with the highest GFP levels (see FIG. 5). These colonies are further cultured without the antibiotic (zeocin) and the GFP signal is determined with intervals of one week, which represent approximately ten cell cycles. The mean of the GFP signal is plotted as in FIG. 3. The first bar of each colony represents the GFP signal at the moment that the antibiotic selection pressure is removed. The adjacent three bars represent the GFP signal that is measured after one, two and three weeks.

Figure 8:
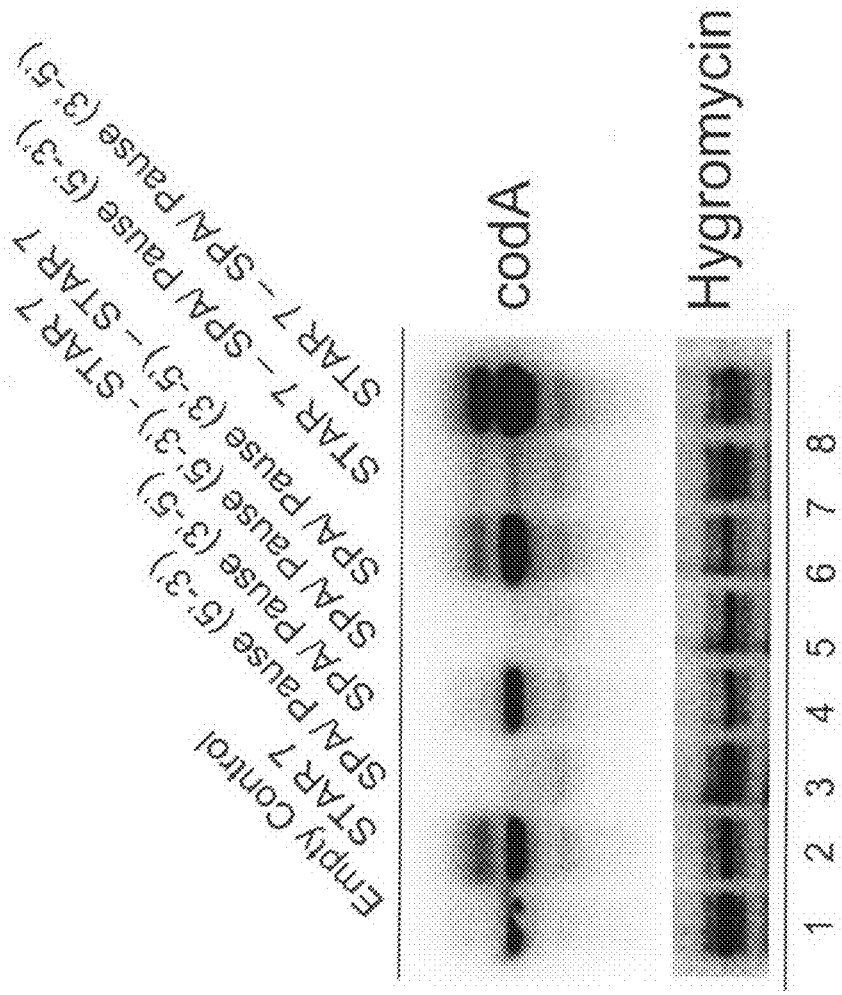

FIG. 8 illustrates TRAPs function in the context of a STAR element. The SPA/pause sequence is placed 5' or 3' of STAR7 and is subsequently tested in the codA vector, after transfection to CHO cells. In this manner, seven different inserts are tested for their ability to block CMV-driven codA transcription; this is in comparison to the signal of the empty vector (lane 1). The following lanes indicate the inserts in the codA constructs: (1) the empty control vector as shown in FIG. 3; (2) STAR7; (3) the SPA/pause sequence in the 5'-3' orientation; (4) the SPA/pause sequence in the 3'-5' orientation; (5) the SPA/pause sequence in the 5'-3' orientation and placed 5' of STAR7; (6) the SPA/pause sequence in the 3'-5' orientation and placed 5' of STAR7; (7) the SPA/pause sequence in the 5'-3' orientation and placed 3' of STAR7; (8) the SPA/pause sequence in the 3'-5' orientation and placed 3' of STAR7. The hygromycin-resistance gene is used as internal control, indicating the number of copies of the plasmids. The SPA/pause sequence functions as a TRAP only when used in the 5'-3' orientation (lanes 3, 5 and 7), either when used alone (lane 3), placed 5' of STAR7 (lane 5) or placed 3' of STAR7 (lane 7). When used in the 3'-5' orientation (lanes 4, 6 and 8), the SPA/pause sequence does not function as a TRAP, irrespective of being used alone or in combination of STAR7.

DETAILED DESCRIPTION OF THE INVENTION

The term "expression" is typically used to refer to the production of a specific RNA product or products, or a specific protein or proteins, in a cell. In the case of RNA products, it refers to the process of transcription. In the case of protein products, it refers to the processes of transcription, translation and optionally post-translational modifications. In the case of secreted proteins, it refers to the processes of transcription, translation, and optionally post-translational modification (e.g., glycosylation, disulfide bond formation, etc.), followed by secretion. In the case of multimeric proteins, it optionally includes assembly of the multimeric structure from the polypeptide monomers. The corresponding verbs of the noun "expression" have an analogous meaning as the noun.

A protein of interest can be any protein and non-limiting examples are enzymes, immunoglobulin chains, therapeutic proteins like anti-cancer proteins or diagnostic proteins.

A protein is herein defined as being either (i) a product obtained by the processes of transcription and translation and possibly, but not necessarily, the product is part of a multimeric protein (for example, a subunit) and/or (ii) a product obtained by the processes of transcription, translation and post-translational modification. The term "multimer" or "multimeric protein" is typically defined as a protein that comprises two or more, possibly non-identical, polypeptide chains ("monomers"). The different monomers in a multimeric protein can be present in stoichiometrically equal or unequal numbers. In either case, the proportion of the monomers is usually fixed by the functional structure of the multimeric protein.

The terms "cell"/"host cell" and "cell line"/"host cell line" are respectively typically defined as a eukaryotic cell and preferably homogeneous populations thereof that are maintained in cell culture by methods known in the art and that have the ability to express heterologous proteins. However, it is clear that the method according to the invention can also be used for protein expression in prokaryotes.

The terms "recombinant (host) cell" and "recombinant (host) cell line" are, respectively, typically defined as a host cell and preferably homogeneous populations thereof into which a transgene has been introduced for the purpose of expression of a gene product, preferably a protein or proteins.

The term "protein expression unit" is herein defined as a unit capable of providing protein expression and typically comprises a functional promoter, an open reading frame encoding a protein of interest and optionally a terminator, all in operable configuration. A functional promoter is a promoter that is capable of initiating transcription in a particular cell. Suitable promoters for obtaining expression in eukaryotic cells are the CMV-promoter, a mammalian EF1-alpha promoter, a mammalian ubiquitin promoter, or a SV40 promoter, or a functional part, derivative and/or analogue thereof having the same function in kind, not necessarily in amount. A functional terminator is capable of providing transcription termination, as in the case of the SV40 terminator. The term "an open reading frame encoding a protein of interest (or a transgene)" is typically defined as a fragment of DNA that codes for a specific RNA product or products or a specific protein or proteins and that is capable of becoming integrated into the genome of a host cell. It includes DNA elements required for proper transcription and, when protein is desired, the necessary elements for translation of the coding region(s) of the transgene. DNA encoding the protein of interest/transgene can either be a DNA encoding a product obtained by the processes of transcription and translation (and possibly, but not necessarily, the product is part of a multimeric protein, for example, a subunit) or a product obtained by the processes of transcription, translation and post-translational modification.

A TRAP sequence is herein functionally defined as a sequence capable of, at least in part, preventing formation of antisense RNA or to, at least in part, prevent transcription to enter the protein expression unit.

In other words a TRAP sequence, when placed into a transcription unit, results in a reduced level of transcription of the nucleic acid present on the 3'-side of the TRAP when compared to the level of transcription observed in the nucleic acid on the 5'-side of the TRAP. When in this application no particular reference is made toward the orientation of the TRAP in a particular construct, it is in the orientation that it blocks transcription from entering a (potential) transcription unit, i.e., the transcription unit of the nucleic acid of interest. Preferably, the TRAP sequence is physically linked to the protein expression unit that it aims to transcriptionally isolate from any flanking transcription units, at least prior to transfecting the unit into the genome of the cell. Upon integration of the unit, the unit and elements linked thereto become linked to sequences in the genome and the element present therein. In the case of concatemer integration, the integrated unit can become linked to co-integrated units or other transfected nucleic acid. In these embodiments, a TRAP can be present upstream or downstream of the transcription unit it aims to isolate. When it is present upstream, the orientation of the TRAP is such that it can, at least in part, reduce transcription originating upstream of the transcription unit and the TRAP and proceeding toward the transcription unit. When it is present downstream of the transcription unit, the TRAP is, in these embodiments, in an orientation that it at least in part reduces transcription origination downstream from the transcription unit that it is linked to and proceeding toward the transcription unit. The orientation upstream or downstream are typically mirror images of each other. However, as mentioned above, in the situation where concatemers are formed upon integration of a protein expression unit in the genome, it is also possible to prevent transcription from entering a flanking co-integrated transcription unit by placement of a TRAP sequence downstream of the protein expression unit in the orientation that it reduces transcription initiating within the protein expression unit. In this embodiment, the TRAP is, prior to integration, physically linked to the transcription unit of which transcription can enter a flanking transcription unit. Through the linkage of the TRAP to the unit prior to integration, this potential is reduced, at least in part. This TRAP sequence is, in addition to normal the transcription termination and/or polyadenylation signals present, a protein expression unit. With respect to the placing of a TRAP in relation to the protein expression unit it intends to protect from incoming transcription, it is understood that the TRAP is preferably placed close to the expression cassette that it intends to transcriptionally isolate. In other words, it is preferred that there are no potentially active promoter elements firing into the protein coding domain between the TRAP and the protein coding domain of the expression unit it intends to transcriptionally isolate, other than the promoter designed to direct transcription in the transcription unit (i.e., necessary to drive the protein of interest).

As disclosed herein further, a TRAP sequence can, for example, be a polyadenylation site and/or a pausing site, where the RNA polymerase II stalls. A TRAP can be derived from any source, as long as efficient termination of transcription is achieved. In one embodiment, a TRAP is identified based on its ability to, at least in part, prevent formation of antisense RNA or to, at least in part, prevent transcription to enter the protein expression unit. Example 1 provides a method to test the effect of putative TRAPs on transcription. It is shown that STAR elements 7, 17 and 40 are poor in blocking transcription.

On the other hand, certain regions of phage λ, as well as a synthetic polyA sequence, fulfill the criteria of a TRAP, since they are all potent blockers of transcription.

In a preferred embodiment, at least one TRAP sequence is located upstream of the promoter and wherein the TRAP sequence is in a 5'-3' orientation. In yet another preferred embodiment, at least one TRAP sequence is located downstream of the open reading frame and wherein the TRAP sequence is in a 3'-5' orientation with respect to the orientation of the open reading frame. It is clear from the examples disclosed herein that the potential of TRAP sequences is orientation-dependent. It is, therefore, clear that the orientation in which a TRAP is applied to flank a transgene can be of importance for its proper functioning. However, it is clear that there are also TRAP sequences that act independent of their orientation.

In a preferred embodiment, the protein expression unit comprises at least two TRAP sequences. A particularly preferred version of the at least two TRAP embodiments is the presence of at least one TRAP upstream and at least one TRAP downstream of the transcription unit of interest. Thus, preferably, at least two TRAP sequences are arranged such that the TRAP sequences are flanking the combination formed by the promoter and the open reading frame. FIG. 2A shows yet another arrangement. However, when multiple protein expression units are present on one and the same part of genetic information, it is also possible to at least partly inhibit or block transcription from one protein expression unit into another protein expression unit. In this case, a TRAP sequence is placed between (possibly different) protein expression units, the orientation of this TRAP sequence is, of course, in the 5'-3' orientation with respect to transcription for which the blocking is intended. In the situation outlined in FIG. 2A, a TRAP sequence is placed between the terminator of the bicistronic gene and the SV40 promoter. In another embodiment, a third TRAP sequence is linked to the expression cassette. When two expression cassettes integrate in a convergent manner (FIG. 1A), transcriptional inert domains can be created by placing TRAP sequences in such a configuration that transcription is prevented to enter the transcription units. This configuration is shown in FIG. 2A. It can, however, be envisioned that the "inertness" of the transcription units can be strengthened when the CMV-driven transcription in the units of FIG. 1A are also prevented from escaping the transcription unit. Normally, the SV40 transcriptional terminator is used for this purpose. This terminator does not, however, stop transcription completely. Hence, a third TRAP sequence is incorporated upstream of the 3' STAR element in the expression cassette (FIG. 2C). This TRAP sequence is placed in a 5'-3' orientation in order to stop transcription that might leak through the SV40 transcriptional terminator. In this configuration, the entire expression cassette has become essentially inert for transcription leaking in, as well as leaking out.

Thus, in another embodiment, the invention provides the use of a TRAP to, at least in part, isolate a genetic element from transcription proceeding into the element. In a preferred embodiment, the genetic element is a STAR element. Thus, the invention further provides a STAR element together with a TRAP sequence of the invention. Preferably, a STAR element is flanked by at least two STAR elements on either side. The orientation of the TRAP element in these embodiments is such that transcription proceeding from outside the STAR element into the STAR element is at least in part prevented. This embodiment is, in particular, relevant if there were to be inverted repeats present in the STAR element. These inverted repeats can initiate the formation of dsRNA. This in turn would lead to gene silencing of adjacent genes. Thus, this specific configuration of TRAP-STAR-TRAP elements not only can prevent formation of dsRNA in the genetic element, i.e., the STAR element, it also provides further protection of the entire expression unit.

TRAPS have a beneficial effect on transgene expression, in particular when high copy numbers are present in a cell. Without being bound to theory, it is believed that high copy numbers signify large amounts of (inverted) repeat sequences, as well as numerous possibilities for transcriptional read-through to occur, this could lead to RNAi and gene silencing.

In yet another embodiment, the invention provides a method for expression of at least one protein of interest in a cell comprising providing the cell with at least one protein expression unit that comprises a promoter functionally linked to an open reading frame encoding at least one protein of interest characterized in that the protein expression unit further comprises at least one TRAP sequence. It is believed that the TRAP sequence at least in part prevents formation of antisense RNA or at least in part prevents transcription to enter the protein expression unit and wherein the protein expression unit further comprises at least one STabilizing Anti-Repressor (STAR) sequence. Non-limiting examples of STAR sequences are shown in Table 2.

A STAR (STabilizing Anti-Repressor) sequence (or STAR element; the terms will be used interchangeably herein) is a naturally occurring DNA element that is disclosed in a co-pending patent application PCT/NL02/00390 (which claims priority from EP 01202581.3; both patent applications are incorporated herein by reference). STAR-sequences can, for example, be identified (as disclosed, for example, in Example 1 of EP 01202581.3) using a method of detecting and optionally selecting a DNA sequence with a gene transcription-modulating quality. However, it is clear from the application that STAR sequences can be obtained in various ways. For such methods and (new) STAR elements resulting therefrom, reference is made to PCT/NL02/00390. A STAR sequence comprises the capacity to influence transcription of genes in cis and/or provide a stabilizing and/or an enhancing effect. The expression level of the transgene is stable over many cell generations and does not manifest stochastic silencing. Therefore, STAR sequences confer a degree of position-independent expression on transgenes that is not possible with conventional transgenic systems. The position independence means that transgenes that are integrated in genomic locations that would result in transgene silencing are, with the protection of STAR elements, maintained in a transcriptionally active state.

In a preferred embodiment, the protein expression unit further comprises at least two STAR sequences. As disclosed herein within the experimental part, TRAP sequences and STAR elements can protect individual transgenes from silencing. Expression units that are not flanked by TRAPs and/or STAR elements can undergo significant silencing after only 5 to 60 culture passages, during which time silencing of the TRAPs and/or STAR element protected units is negligible. The present invention preferably uses TRAP and STAR sequences for the production of one or more proteins and thereby, the invention provides (1) an increased predictability in the creation of recombinant cell lines that efficiently produce the heterologous protein of interest, (2) an increased yield of the heterologous protein, (3) stable expression of the heterologous protein, even during prolonged cultivation in the absence of selection agent, (4) the invention also provides favorable transgene expression characteristics without amplification of the transgene. The increased yield of a heterologous protein provided by the invention may be obtained at low transgene copy numbers, without selective co-amplification using, for example, the DHFR/methotrexate system. This results in greater stability since the transgene copy number is low and is not susceptible to decrease due to recombination (McBurney et al. 2002) or repeat-induced gene silencing (Garrick et al. 1998) and/or (5) the broad applicability of the method of the invention includes its utility in a wide range of host cell lines. This is, for example, useful/desirable when a particular protein is preferably expressed by a particular host cell line (e.g., expression of antibodies from lymphocyte-derived host cell lines). The above-mentioned advantages are not only relevant to the expression of a single protein in a cell. The combination of a TRAP with a STAR element is particularly favorable when a multimeric protein is to be expressed in the cell. The increased predictability of foreign gene expression that is obtained by using this combination results in a significantly higher number of cells that efficiently produce the multimeric protein, higher yields of multimeric protein can be obtained, cell lines more stability produce the multimeric protein even in the absence of selection pressure, there is no need for amplification and/or it can be used in a wide variety of cell lines.

The use of TRAPs and/or STARs to flank at least one protein expression unit is one of the aspects of the balanced and proportional levels of expression of one or more proteins and, more specifically, for the expression of the monomers of multimeric proteins. The TRAPs and STARs create chromatin domains of definite and stable transcriptional potential. As a result, promoters that drive transcription of monocistronic or bicistronic mRNA function at definite stable levels. A recombinant host cell line created by the method of the invention is readily identified in which these levels result in appropriate proportions of each monomer of the multimeric protein of interest being expressed at high yields.

Use of STARs and TRAPs is thought to prevent silencing of transgene expression by combined action of keeping chromatin-associated repression out (STAR elements) and by simultaneously creating domains from which aberrant and harmful transcription is kept out (TRAPs). A TRAP element in orientation of the present invention provides for more stable expression of the heterologous transgene, particularly in the context of a STAR element.

Preferably, at least two STAR sequences are arranged such that the STAR sequences are flanking the combination formed by the promoter and the open reading frame (as outlined in FIG. 2A). Even more preferably, at least two TRAP sequences and at least two STAR elements are arranged such that a first 5' TRAP sequence is upstream of a first STAR sequence and that a second 3' TRAP sequence is downstream of a second STAR sequence.

FIG. 2 provides a non-limiting schematic representation of one of the embodiments of this part of the invention. This is the configuration of the DNA elements of the expression units in the nucleic acid as well as after integration into the genome. Expression unit one is shown in FIG. 2A. It contains an open reading frame for a transgene (a reporter gene, Gene 1). This is upstream of the attenuated EMCV IRES (Martinez-Sals et al. 1999, Mizuguchi et al. 2000, Rees et al. 1996) and of the open reading frame encoding the zeocin-resistance selectable marker protein (zeo). The gene has the SV40 transcriptional terminator at it 3' end (t). This bicistronic transgene is transcribed at high levels from the CMV promoter. Next to this is the puromycin-resistance selectable marker (puro), transcribed as a monocistronic mRNA from the SV40 promoter. The gene has the SV40 transcriptional terminator at its 3' end (t). STAR elements flank the expression units. The entire cassette with multiple genes plus STARs is flanked by TRAPs in such an orientation that transcription can be prevented to enter the expression units on the nucleic acid or a TRAP is orientated such that little or no anti-sense RNA is formed. To further improve expression, a TRAP sequence and/or a STAR sequence is placed between the bicistronic and the monocistronic gene.

In FIG. 2B, another configuration of expression units is depicted. The construct consists of two transgenes (two reporter genes or the open reading frames for two subunits of a heterodimeric protein (Gene 1 and Gene 2) of which Gene 1 is upstream of the attenuated EMCV IRES and the puromycin-resistance protein (puro) and Gene 2 is upstream of the EMCV IRES and the zeocin-resistance protein (zeo). These bicistronic transgenes are transcribed at high levels from the CMV promoter, which are directed in different orientations to prevent transcriptional interference. Both bicistronic genes have the SV40 transcriptional terminator at their 3' ends (t). STAR elements flank the expression units. The entire cassette with multiple genes plus STARs is flanked by TRAPs in such an orientation that transcription can be prevented to enter the expression units on the nucleic acid or orientated such that little or no anti-sense RNA is formed.

It is clear to a person skilled in the art that the sequence in which the TRAPs and STARs are placed to flank the expression units can vary. In the given example, the STARs are placed between the expression unit and the TRAPs. However, it is also possible to place the TRAPs between the expression unit and the STAR element.

It is also clear to a person skilled in the art that other selection markers and other combinations of selection markers are possible. Examples of possible antibiotic combinations are provided herein. The one antibiotic that is particularly advantageous is zeocin, because the zeocin-resistance protein (zeocin-R) acts by binding the drug and rendering it harmless. Therefore, it is easy to titrate the amount of drug that kills cells with low levels of zeocin-R expression, while allowing the high expressors to survive. All other antibiotic-resistance proteins in common use are enzymes and, thus, act catalytically (not 1:1 with the drug). When a two-step selection is performed, it is, therefore, advantageous to use an antibiotic-resistance protein with this 1:1 binding mode of action. Hence, the antibiotic zeocin is a preferred selection marker. For convenience, the zeocin antibiotic is, in a two-step selection method, combined with puromycin-R or blasticidin-R in the second bicistronic gene and puromycin-R or hygromycin-R in the monocistronic gene.

It is also clear to a person skilled in the art that different promoters can be used as long as they are functional in the used cell. The CMV promoter is considered the strongest available, so it is preferably chosen for the bicistronic gene in order to obtain the highest possible product yield. Other examples of suitable promoters are, e.g., mammalian promoters for EF1-alpha or ubiquitin C promoter. The good expression and stability of the SV40 promoter makes it well suited for expression of the monocistronic gene; enough selection marker protein (for example, the antibiotic-resistance protein puromycin-R in the example cited herein) is made to confer high expression of the selection marker. Hence, the SV40 promoter is preferentially used as a promoter driving the expression of the selection marker.

In a preferred embodiment, the invention provides a method for expression of at least one protein of interest, further comprising providing the cell with a second protein expression unit. This is particularly advantageous when two proteins (for example, two monomers) need to be expressed according to a method of the invention.

Preferably, at least one of the protein expression units comprises a monocistronic gene comprising an open reading frame encoding the protein of interest and wherein the monocistronic gene is under control of a functional promoter. The term "monocistronic gene" is typically defined as a gene capable of providing a RNA molecule that encodes one protein/polypeptide. In yet another preferred embodiment, a monocistronic gene is used for expression of a selection marker. One example is provided in FIG. 2A wherein a puromycin gene is cloned behind an SV40 promoter.

In yet another preferred embodiment, at least one of the protein expression units comprises a bicistronic gene comprising an open reading frame encoding the protein of interest, a protein translation initiation site with reduced translation efficiency, a selection marker and wherein the bicistronic gene is under control of a functional promoter. The term "bicistronic gene" is typically defined as a gene capable of providing a RNA molecule that encodes two proteins/polypeptides.

As outlined above, the method according to the invention can comprise at least two TRAP sequences and at least two STAR sequences. Preferably, at least two TRAP sequences are essentially identical. Even more preferably, at least two STAR sequences are essentially identical.

Essentially identical TRAP and/or STAR sequences are defined herein as TRAP and/or STAR sequences that are identical in their important domains (the domains that confer the transcription-stabilizing or -enhancing quality) but that may vary within their less important domains, for example, a point mutation, deletion or insertion at a less important position within the TRAP and/or STAR sequence. Preferentially, the essentially identical TRAP and/or STAR sequences provide equal amounts of transcription-stabilizing or -enhancing activity. Examples of suitable TRAP and/or STAR sequences are outlined in the experimental part herein.

Yet another preferred feature of the method according to the invention is the introduction of a (weak) Internal Ribosome Binding Site (IRES) as an example of a protein translation initiation site with a reduced translation efficiency, between the open reading frame of the protein of interest and the selection marker open reading frame. In combination with, for example, the TRAP and/or STAR sequence, this component of the present invention comprises a marked improvement in transgenic systems for the expression of two or more proteins.

Internal ribosome binding site (IRES) elements are known from viral and mammalian genes (Martinez-Salas 1999) and have also been identified in screens of small synthetic oligonucleotides (Venkatesan and Dasgupta 2001). The IRES from the encephalomyocarditis virus has been analyzed in detail (Mizuguchi et al. 2000). An IRES is an element encoded in DNA that results in a structure in the transcribed RNA at which eukaryotic ribosomes can bind and initiate translation. An IRES permits two or more proteins to be produced from a single RNA molecule (the first protein is translated by ribosomes that bind the RNA at the cap structure of its 5' terminus (Martinez-Salas 1999)). Translation of proteins from IRES elements is less efficient than cap-dependent translation: the amount of protein from IRES-dependent open reading frames (ORFs) ranges from less than 20% to 50% of the amount from the first ORF (Mizuguchi et al. 2000). This renders IRES elements undesirable for production of all subunits of a multimeric protein from one messenger RNA (mRNA), since it is not possible to achieve balanced and proportional expression of two or more protein monomers from a bicistronic or multicistronic mRNA. However, the reduced efficiency of IRES-dependent translation provides an advantage that is exploited by the current invention. Furthermore, mutation of IRES elements can attenuate their activity and lower the expression from the IRES-dependent ORFs to below 10% of the first ORF (Lopez de Quinto and Martinez-Salas 1998, Rees et al. 1996). The advantage exploited by the invention is as follows: when the IRES-dependent ORF encodes a selectable marker protein, its low relative level of translation means that high absolute levels of transcription must occur in order for the recombinant host cell to be selected. Therefore, selected recombinant host cell isolates will, by necessity, express high amounts of the transgene mRNA. Since the recombinant protein is translated from the cap-dependent ORF, it can be produced in abundance resulting in high product yields.

It is clear to a person skilled in the art that changes to the IRES can be made without altering the essence of the function of the IRES (hence, providing a protein translation initiation site with a reduced translation efficiency), resulting in a modified IRES. Use of a modified IRES that is still capable of providing a small percentage of translation (compared to a 5' cap translation) is, therefore, also included in this invention.

When the method according to the invention is used for the expression of two or more proteins encoded by different protein expression units, preferably, each of the protein expression units resides on a separate DNA carrier. In each transcription unit, the monomer ORF is produced by efficient cap-dependent translation. This feature of the invention contributes that recombinant host cells are isolated that have high yields of each monomer at levels that are balanced and proportionate to the stoichiometry of the multimeric protein. The increased predictability at which such recombinant host cells are isolated results in an improvement in the efficiency of screening for such isolates by a factor of ten or more. In a preferred embodiment, the DNA carrier is a vector (or a recombinant or isolated nucleic acid, a preferred vector is a plasmid; the terms are used interchangeably herein). In another embodiment, the vector is a viral vector and in a more preferred embodiment, the viral vector is an adenoviral vector or a retroviral vector. It is clear to persons skilled in the art that other viral vectors can also be used in the method according to the invention.

Conventional expression systems are DNA molecules in the form of a recombinant plasmid or a recombinant viral genome, although other means exist that are in no way excluded. The nucleic acid, preferably a plasmid or the viral genome, is introduced into (mammalian host) cells and integrated into their genomes by methods known in the art. The present invention also uses these types of DNA molecules to deliver its improved transgene expression system. A preferred embodiment of the invention is the use of nucleic acid, preferably plasmid DNA for delivery of the expression system. A plasmid contains a number of components: conventional components, known in the art, are an origin of replication and a selectable marker for propagation of the plasmid in bacterial cells; a selectable marker that functions in eukaryotic cells to identify and isolate host cells that carry an integrated transgene expression system; the protein of interest, whose high-level transcription is preferably brought about by a promoter that is functional in the host cell (e.g., the human cytomegalovirus major immediate early promoter/enhancer, pCMV (Boshart et al. 1985)); and viral transcriptional terminators (e.g., the SV40 polyadenylation site (Kaufman & Sharp 1982)) for the transgene of interest and the selectable marker.

The vector used can be any vector that is suitable for, for instance, cloning DNA and that can be used in a transcription system. When host cells are used, it is preferred that the vector is an integrating vector; however, an episomally replicating vector can also be used. In an episomal vector, effects due to different sites of integration of the vector are avoided. DNA elements flanking the vector at the site of integration can have effects on the level of transcription of the promoter and thereby mimic effects of fragments comprising DNA sequences with a gene transcription modulating quality. In a preferred embodiment, the vector comprises a replication origin from the Epstein-Barr virus (EBV), OriP, and a nuclear antigen (EBNA-1). Such vectors are capable of replicating in many types of eukaryotic cells and assemble into chromatin under appropriate conditions. Another method for, at least in part, reducing effects of the site of integration on the expression unit is to use one or more of the previously mentioned STAR elements. Thus, the invention further provides a vector comprising a TRAP element and a STAR element, preferably in combination with an expression unit.

Preferably, the method according to the invention is used to express/produce at least one immunoglobulin chain as the at least one protein of interest, for example, an immunoglobulin heavy chain or an immunoglobulin light chain. According to this embodiment, a multimeric protein, an antibody, is obtained. It is clear to a person skilled in the art that it is possible to provide a cell that expresses an immunoglobulin heavy chain from one protein expression unit and an immunoglobulin light chain from another protein expression unit with a third protein expression unit encoding a secretory component or a joining chain. In this way, the production of, for example, sIgA and pentameric IgM is provided. Preferably, the first protein of interest and the second protein of interest comprise at least the variable part of an immunoglobulin light chain and immunoglobulin heavy chain. Preferably the first protein of interest comprises at least the variable part of an immunoglobulin heavy chain, whereas the second protein of interest comprises an immunoglobulin light chain or derivative and/or analogue thereof. This embodiment warrants that an increased proportion of the cells will display a tendency to slightly overproduce immunoglobulin heavy chain, thereby allowing more efficient production of a multimeric protein. Immunoglobulin technology is very advanced at the present time and it is possible to generate coding domains for antibodies that have no complementary antibody in nature, i.e., a completely artificial antibody. Such antibodies are also within the scope of the present invention. For an overview of relevant technology for antibodies, their selection and production, we refer to H. E. Chad and S. M. Chamow 2001.

Improvements provided by the method according to the invention have three integrated aspects. (1) With existing systems, recombinant cell lines that simultaneously express acceptable quantities of the monomers of multimeric proteins can be created only at very low frequencies; the present invention increases the predictability of creating high-yielding recombinant host cell lines by a factor of ten or more. (2) Existing systems do not provide stoichiometrically balanced and proportional amounts of the subunits of multimeric proteins; the present invention ensures that the expression levels of the subunits will be balanced and proportional. (3) Existing systems do not provide a means of protecting the transgenes that encode the protein subunits from transgene silencing.

Example 1 provides a method for identifying a TRAP sequence and, hence, in another embodiment, the present invention also provides a method for identifying a TRAP sequence comprising providing a cell with a nucleic acid, preferably a plasmid that comprises a promoter sequence, an intervening sequence (IV) downstream of the promoter, a putative TRAP sequence located in the IV, a sequence whose product is detectable and which sequence is located downstream of the IV, determining the amount of the detectable product and compare the amount with the amount of product obtained in a cell that is provided with a control nucleic acid, preferably a plasmid without the putative TRAP sequence.

The cloning of the putative TRAP sequence is performed in the intervening sequence to avoid the possibility that addition of a sequence results in enhanced RNA instability. This would also result in a lower RNA signal on a blot, but this would have nothing to do with blocking of transcription. Placing the to-be-tested sequence in intervening sequences results in the transcription of this sequence into RNA, but it is subsequently spliced out, so a functional, in this particular case codA, mRNA is formed. This happens irrespective whether or not there was an extra sequence within the intervening sequence. Any decline in the mRNA signal is, therefore, not due to loss of RNA stability, but a direct consequence of transcription termination due to the TRAPs sequence.

In a preferred embodiment, the invention provides a method for identifying a TRAP sequence comprising providing a cell with a nucleic acid, preferably a plasmid that comprises a promoter sequence; an intervening sequence (IV) downstream of the promoter; a putative TRAP sequence located in the IV; a sequence whose product is detectable and which sequence is located downstream of the IV; the nucleic acid, preferably a plasmid, further comprises a selection marker located outside the combination of the promoter, IV, putative TRAP and the sequence whose product is detectable; selecting a cell via the selection marker of the nucleic acid, preferably a plasmid, thereby obtaining a cell that comprises the nucleic acid, preferably a plasmid; determining the amount of the detectable product and compare the amount with the amount of product obtained in a cell that is provided with a control nucleic acid, preferably a plasmid without the putative TRAP sequence.

The term "selection marker or selectable marker" is typically used to refer to a gene and/or protein whose presence can be detected directly or indirectly in a cell, for example, a gene and/or a protein that inactivates a selection agent and protects the host cell from the agent's lethal or growth-inhibitory effects (e.g., an antibiotic resistance gene and/or protein). Another possibility is that the selection marker induces fluorescence or a color deposit (e.g., green fluorescent protein and derivatives, luciferase, or alkaline phosphatase).

The term "selection agent" is typically defined as a chemical compound that is able to kill or retard the growth of host cells (e.g., an antibiotic).

The term "selection" is typically defined as the process of using a selection marker/selectable marker and a selection agent to identify host cells with specific genetic properties (e.g., that the host cell contains a transgene integrated into its genome).

Preferably, the invention provides a method wherein the sequence whose product is detectable is a suicide gene. A suicide gene is typically defined as a gene which product is capable of killing a cell, either directly or indirectly. More preferably, the suicide gene is codA or codA::upp. Even more preferably, the detectable product is mRNA. However, it is clear to a person skilled in the art that a protein can also be used as a detectable product. In this case, amounts/levels of protein are determined by, for example, Western blotting or by detecting the protein directly, for example, GFP, or by performing an enzymatic (color) reaction based on the properties of the corresponding protein.

Use of a suicide gene, for example, coda or codA::upp is particularly advantageous for the screening of a library of sequences. When sequences of a library are cloned in the intervening sequence (IV), a TRAP sequence is easily identified because the suicide gene is not transcribed and translated and, hence, the lethal product of the suicide gene is not produced and the cell that comprises the TRAP sequence survives. When the cloned sequence is not a TRAP sequence, the cell dies because of the lethal-formed product. It is clear that different types of suicide genes can be used. The coda gene encodes the enzyme cytosine deaminase that converts cytosine to uracil. CodA can be used as a metabolic suicide gene in combination with the prodrug 5-fluorocytosine. The enzyme is able to convert the non-toxic prodrug into 5-fluorouracil-mono phosphate that kills the cells by disrupting DNA synthesis, thereby triggering apoptosis. CodA::upp is a fusion between a cytosine deaminase gene and a uracil phosphoribosyl transferase gene. Both enzymes act synergistically to convert 5-fluorocytosine into fluorouracil-mono phosphate, a toxic compound. The fusion of the genes leads to a more efficient system. Another example of a suicide gene and a non-toxic prodrug is thymidine kinase and ganciclovir. However, it is clear that it is also possible to use a suicide gene that is not dependent on the presence of a prodrug.

Hence, the invention also provides a method for identifying a TRAP sequence comprising providing a cell with a nucleic acid, preferably a plasmid that comprises a promoter sequence, an intervening sequence (IV) downstream of the promoter, a putative TRAP sequence located in the IV, a sequence encoding a suicide product and is located downstream of the IV, determining whether the cell survives.

Preferably, the putative TRAP sequence is derived from a library. In yet another preferred embodiment, a prodrug is used that is converted into a toxic compound by the product of the suicide gene.

In Example 1, the codA::upp open reading frame is used as a sequence whose product is detectable and the amount of RNA is determined.

It is clear that the invention also provides a TRAP sequence obtainable by the method according to the invention. Preferred examples of the TRAP sequences are outlined in the experimental part and in Table 1. Preferably, the TRAP sequence comprises the lambda 35711-38103 sequence as depicted in Table 1 and/or a functional equivalent and/or a functional fragment thereof. In another preferred embodiment, the TRAP sequence comprises a polyA sequence, preferably a synthetic polyA (SPA) sequence and/or a functional equivalent and/or a functional fragment thereof, for example, a SPA sequence and/or a functional equivalent and/or a functional fragment thereof as depicted in Table 1. In yet another preferred embodiment, aid TRAP sequence comprises a combination of an SPA and the human α2 globin gene pause signal and/or a functional equivalent and/or a functional fragment thereof, for example, a combination of a SPA and the human α2 globin gene pause signal and/or a functional equivalent and/or a functional fragment as depicted in Table 1.

A functional equivalent and/or a functional fragment of a sequence depicted in Table 1 or 2 is defined herein as follows. A functional equivalent of a sequence as depicted in Table 1 or 2 is a sequence derived with the information given in Table 1 or 2. For instance, a sequence that can be derived from a sequence in Table 1 by deleting, modifying and/or inserting bases in or from a sequence listed in Table 1 or 2, wherein the derived sequence comprises the same activity in kind, not necessarily in amount, of a sequence as depicted in Table 1 or 2. A functional equivalent is further a sequence comprising a part from two or more sequences depicted in Table 1 or 2. A functional fragment of a sequence in Table 1 or 2 can, for example, be obtained by deletions from the 5' end or the 3' end or from inside of the sequences or any combination thereof, wherein the derived sequence comprises the same activity in kind, but not necessarily in amount.

In yet another embodiment, the invention provides the use of a TRAP sequence for, at least in part, preventing entering transcription into a protein expression unit or use of a TRAP sequence for, at least in part, preventing formation of antisense RNA. Preferably the TRAP sequence is selected from the sequences depicted in Table 1. Even more preferably, the TRAP sequence is combined with a STAR sequence as depicted in Table 2. Use according to the invention is particularly advantageous when applied to expression of at least one protein of interest.

In yet another embodiment, the invention provides a protein expression unit that comprises a promoter functionally linked to an open reading frame encoding a protein of interest, characterized in that the protein expression unit further comprises at least one TRAP sequence, wherein the TRAP sequence at least in part prevents transcription to enter the protein expression unit or wherein the TRAP sequence at least in part prevents formation of antisense RNA. In a preferred embodiment, at least one TRAP sequence is located upstream of the promoter and wherein the TRAP sequence is in a 5'-3' orientation. In yet another preferred embodiment, at least one TRAP sequence is located downstream of the open reading frame and wherein the TRAP sequence is in a 3'-5' orientation. Even more preferred, the protein expression unit comprises at least two TRAP sequences. Preferably, at least two TRAP sequences are arranged such that the protein expression unit is flanked on either side by at least one TRAP sequence.

In another preferred embodiment, the protein expression unit further comprises at least one STabilizing Anti-Repressor (STAR) sequence. In an even more preferred embodiment, the protein expression unit further comprises at least two STAR sequences. Preferably, at least two STAR sequences are arranged such that the STAR sequences are flanking the combination formed by the promoter and the coding region. Even more preferably, at least two TRAP sequences and at least two STAR sequences are arranged such that a first 5' TRAP sequence is upstream of a first STAR sequence and that a second 3' TRAP sequence is downstream of a second STAR sequence.

In yet another preferred embodiment, the invention provides a protein expression unit, wherein at least two TRAP sequences are essentially identical and/or at least two STAR sequences are essentially identical.

In a preferred embodiment, the protein expression unit of the invention is provided, wherein the protein of interest is an immunoglobulin heavy chain. In yet another preferred embodiment, the protein expression unit of the invention is provided, wherein the protein of interest is an immunoglobulin light chain. When these two protein expression units are present within the same (host) cell a multimeric protein and, more specifically, an antibody is assembled.

In yet another embodiment, the invention provides a protein expression unit that comprises a TRAP sequence and wherein the TRAP sequence at least in part prevents transcription entering into the protein expression unit or wherein the TRAP sequence at least in part prevents formation of antisense RNA. The invention also includes a (host) cell comprising at least one protein expression unit according to the invention. Such a (host) cell is then, for example, used for large-scale production processes.

The invention also includes a cell obtainable according to any one of the methods as described herein.

In a preferred embodiment, the cell of the invention is a plant cell. RNAi plays an important role in plant cells and hence, applying the method according to the invention to a plant cell is particularly advantageous. Examples of a dicot plant cell are a potato cell, a tomato cell or an *Arabidopsis* cell. Examples of a monocot cell are a rice cell, a wheat cell or a barley cell.

The invention furthermore includes a protein obtainable from the cell (for example, via the process of protein purification). Preferably, the protein is a multimeric protein and even more preferably, the multimeric protein is an antibody. Such an antibody can be used in pharmaceutical and/or diagnostic applications.

In yet another embodiment, the invention provides a cell line comprising a cell as described above. Preferably, the cell line comprises a U-2 OS osteosarcoma, CHO, 293, HuNS-1 myeloma, WERI-Rb-1 retinoblastoma, BHK, Vero, non-secreting mouse myeloma Sp2/0-Ag 14, non-secreting mouse myeloma NSO, or NCI-H295R adrenal gland carcinoma cell line.

A cell or the cell line of the invention is particularly advantageous when used for the production of a proteinaceous molecule.

The invention also provides a protein obtainable by the method according to the invention. Preferably, the protein is an immunoglobulin chain. Even more preferably, the protein is a multimeric protein. An example of a multimeric protein is an antibody.

Furthermore, the invention also provides a method for producing a protein of interest comprising culturing a cell or the cell line of the invention and harvesting the protein of interest from the corresponding culture.

The foregoing discussion and the following examples are provided for illustrative purposes and they are not intended to limit the scope of the invention as claimed herein. They simply provide some of the preferred embodiments of the invention. Modifications and variations, which may occur to one of ordinary skill in the art, are within the intended scope of this invention. Various other embodiments apply to the present invention, including: other selectable marker genes; other IRES elements or means of attenuating IRES activity; other elements affecting transcription including promoters, enhancers, introns, terminators, and polyadenylation sites; other orders and/or orientations of the monocistronic and bicistronic genes; other anti-repressor elements or parts, derivations, and/or analogues thereof; other vector systems for delivery of the inventive DNA molecules into eukaryotic host cells; and applications of the inventive method to other transgenic systems.

The invention is further explained with the aid of the following illustrative Examples.

EXPERIMENTAL PART AND RESULTS

Example 1

Identification of TRAnscription Pause (TRAP) Sequence

The invention may be used to identify DNA elements that act as TRAnscription Pause sequences. In this example, we provide a method for identifying TRAP sequences.
Materials and Methods
Plasmids For constructing pIRES-6, pIRES (Clontech) is taken as a starting plasmid. pIRES is cut with BglII and DraI, and the CMV promoter, intervening sequence (IV), IRES and SV40 polyadenylation signal ligated into pBSKS (Stratagene), cut with BamHI and EcoRV to create pIRES-1. Oligos STOP 1 (CTAGCTAAGTAAGTAAGCTTGG (SEQ ID NO:1)) and STOP 2 (AATTCCAAGCTTACTTA CTTAG (SEQ ID NO:2)) are ligated into NheI-XhoI cut pIRES1, creating pIRES-2. This results in three stop codons, in three different reading frames, in front of the IRES. Oligos BamHI-BglII-AscI (TTAAGGATCCAGATCTGGCGCGCC (SEQ ID NO:3)) and AscI-BglII-BamHI (TTAAGGCGCGCCA-GATCTGGATCC (SEQ ID NO:4)) are annealed and ligated into BsaI cut pIRES-2, creating pIRES-3. In this way, AscI, BamHI and BglII sites are created in the intervening sequences. pORFCODA::UPP (InvitroGen) is cut with NcoI-NheI, filled in with Klenow, and ligated 3' of the IRES, into the SmaI of pIRES-3, creating pIRES-4. The cloning is performed in the intervening sequence to avoid the possibility that addition of a sequence results in enhanced RNA instability. This would also result in a lower RNA signal on a blot, but this would have nothing to do with blocking of transcription. Placing the to-be-tested sequence in intervening sequences results in the transcription of this sequence into RNA, but it is subsequently spliced out, so a functional codA mRNA is formed. This happens irrespective of whether there was an extra sequence within the intervening sequence or not. Any decline in the mRNA signal is, therefore, not due to loss of RNA stability, but a direct consequence of transcription termination due to the TRAPs sequence.

Next, pIRES-4 is cut with XhoI-XbaI, filled in with Klenow, and ligated into SmaI cut pBSKS, creating pIRES-5. pIRES 5 is cut with SalI, and ligated into pPURO partially digested with SalI, creating pIRES-6. Thus, the whole cassette consists of the CMV promoter, the IV, IRES, codA::upp and SV40 polyadenylation signal in a pREP4 (Invitrogen) backbone. In this backbone, a hygromycin-resistance gene is present, to allow selection of transformants on hygromycin.

To create pIRES-31, the IRES and codA::upp in pIRES-6 is replaced by codA::upp only. Oligos NotI-BclI-EV (GGC-CGCTGATCAGATATCGCGG (SEQ ID NO:5)) and NheI-EcoRV-BclI (CTAGCCGCGATATCTGATCAGC (SEQ ID NO:6)) are annealed and ligated to NotI-NheI digested pIRES 6, which releases the IRES and codA::upp. This creates pIRES-30. The CodA::upp ORF as a BamHI fragment is then ligated into BclI cut pIRES-30, creating pIRES-31 (FIG. 3).
Transfection and Culture of U-2 OS Cells Transfection and culture of U-2 OS cells with pIRES-6 and pIRES-31 plasmids: The human osteosarcoma U-2 OS cell line (ATCC #HTB-96) is cultured in Dulbecco's Modified Eagle Medium+10% Fetal Calf Serum containing glutamine, penicillin, and streptomycin (supra) at 37° C./5% $CO_2$. Cells are transfected with the pIRES-6 and -31 vector containing putative TRAPs in MCSI using SuperFect™. Hygromycin selection is complete in two weeks, after which time, a pool of hygromycin-resistant U-2 OS clones are isolated and RNA is isolated using conventional protocols (Sambrook et al. 1989).
Results Several constructs are transfected to U-2 OS cells:
(1) The empty control vector as shown in FIG. 3;
(2) A 2400 bp long DNA of phage λ (bp 35711-38103) in 5'-3' orientation;
(3) A 2400 bp long DNA of phage λ (bp 35711-38103) in 3'-5' orientation;
(4) The 60 bp long MAZ DNA sequence;
(5) STAR7;
(6) STAR40;
(7) The empty control vector as shown in FIG. 3;
(8) A 50 bp long synthetic poly A (SPA) sequence in 5'-3' orientation;
(9) A combination of the 50 bp long SPA sequence and a 92 bp long α2 globin gene pause signal in orientation 5'-3';
(10) A 50 bp long synthetic poly A sequence in 3'-5' orientation; and
(11) A combination of the 50 bp long SPA sequence and a 92 bp long α2 globin gene pause signal in 3'-5' orientation.

Afterwards, transfection selection is performed by hygromycin. After three weeks, the entire pool of cells are harvested and mRNA is isolated. The entire pool of cells is used and no individual colonies since the FIG. 3 vector replicates episomally, which prevents position effects that would occur when the vectors stably integrate.

Figure 4:
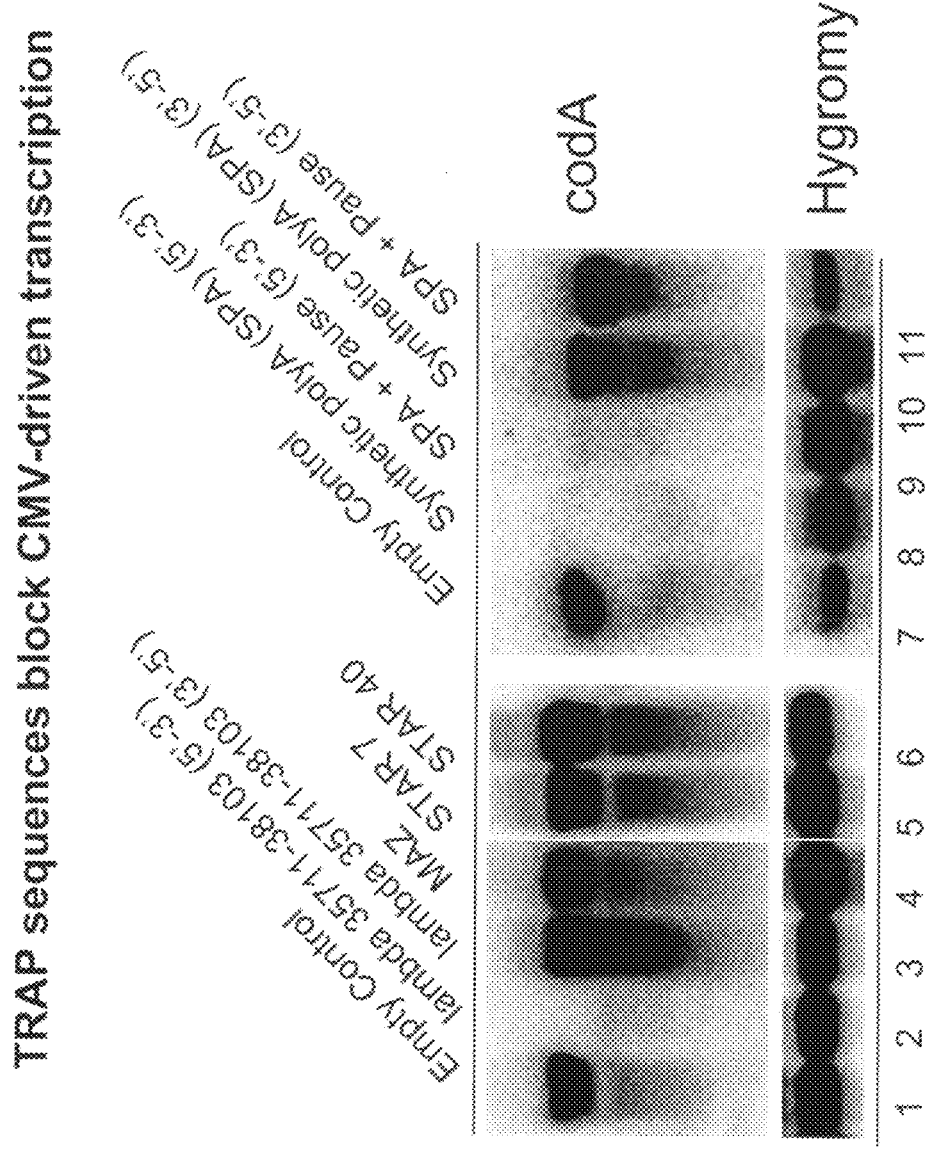
FIG. 4 shows TRAPs efficiently block CMV promoter-driven transcription. Indicated constructs with potential TRAPs that are located between the CMV promoter and the coda gene are transfected to U-2 OS cells. (1) The empty control vector without sequences between the CMV promoter and the coda gene (FIG. 3); (2) A 2400 bp long DNA of phage λ (bp 35711-38103) in 5'-3' orientation; (3) A 2400 bp long DNA of phage λ (bp 35711-38103) in 3'-5' orientation; (4) The 60 bp long MAZ DNA sequence (Ashfield et al. 1994); (5) STAR7; (6) STAR40; (7) the empty control vector as shown in FIG. 3; (8) a 50 bp long synthetic poly A (SPA) sequence (Levitt et al. 1989) in 5'-3' orientation; (9) A combination of the 50 bp long SPA sequence and a 92 bp long α2 globin gene pause signal in 5'-3' orientation; (10) a 50 bp long synthetic poly A sequence in 3'-5' orientation; (11) a combination of the 50 bp long SPA sequence and a 92 bp long α2 globin gene pause signal in 3'-5' orientation.

As shown in FIG. 4, the lambda (bp 35711-37230) (lane 2) fragment efficiently blocks transcription of the codA gene driven by the CMV promoter, as compared to the empty control (lanes 1 and 7). Also, a long synthetic polyA (SPA) sequence (Levitt et al. 1989) (AATAAAAGATCCT-TATTTTCACTAGTTCTGTGTGTTGGTTTTTTGTGTG (SEQ ID NO:7)) either alone (lane 8) or in combination with a 92 bp pausing signal from the human α2 globin gene (AA-CATACGCTCTCCATCAAAACAAAAC-GAAACAAAACAAACTAGCAAA ATAGGCTGTC-CCCAGTGCAAGTGCAGGTGCCAGAACATTTCTCT (SEQ ID NO:8)) (Enriquez-Harris et al. 1991) (lane 9) potently blocks transcription of the codA gene driven by the CMV promoter. The hygromycin-resistance gene is used as internal control, indicating the number of copies of the plasmids. The 60 bp long MAZ sequence has been reported to be a powerful transcription blocker (Ashfield et al. 1994). However, in our test system, the MAZ sequence (lane 4) does not prevent transcription. Also, STAR7 (lane 5) and STAR40 (lane 6) do not prevent transcription of the codA gene driven by the CMV promoter. Quantification of the signals using a phosphoimager showed that the phage lambda (bp 35711-38103), the SPA sequence and the SPA/Pause combination block 95% of the CMV promoter-driven transcription. We conclude that the phage lambda (bp 35711-38103) fragment and the SPA, SPA/Pause sequences (Table 1) serve as TRAP.

Example 2

TRAP Sequences Block Transcription in a Directional Fashion

Materials and Methods

The experiments of Example 1 are referred to.

Results

As shown in FIG. 4, the orientation of the TRAP is an essential parameter in the action of TRAP sequences. The phage lambda (bp 35711-38103) serves only as TRAP in one 5'-3' orientation (lane 2). When tested in the opposite 3'-5' orientation (lane 3), no blocking of CMV-driven transcription is found at all. Similarly, the SPA and the combined SPA/Pause sequence block transcription only in the 5'-3' orientation (lanes 8 and 9) and not in the 3'-5' orientation (lanes 10 and 11). The orientation dependency of TRAP sequences is of importance for the orientation in which they can be used when flanking transgenes.

Example 3

TRAPs Improve the Effects of STAR Elements on the Expression Level of Transgenes One object of this invention is to improve transgene expression for heterologous protein production, thus increasing the yield of the heterologous protein.

Materials and Methods

Plasmids

The construction of the Plug&Play-d2EGFP-ires-Zeo (PP) vector is described below. Plasmid pd2EGFP (Clontech 6010-1) is modified by insertion of a linker at the BsiWI site to yield pd2EGFP-link. The linker (made by annealing oligonucleotides GTACGGATATCAGATCTTTAATTAAG (SEQ ID NO:9) and GTACCTTAATT AAAGATCTGATAT (SEQ ID NO:10)) introduces sites for the PacI, BglII, and EcoRV restriction endonucleases. This creates the multiple cloning site MCSII for insertion of STAR elements. Then primers (GATCAGATCTGGCGCGCCATTTAAATCGTCTCGCGCGTTTCG GTGATGACGG (SEQ ID NO:11)) and (AGGCGGATCCGAATGTATTTAGAAAAATAAACAAATAGGGG (SEQ ID NO:12)) are used to amplify a region of 0.37 kb from pd2EGFP, which is inserted into the BglII site of pIRES (Clontech 6028-1) to yield pIRES-stuf. This introduces sites for the AscI and SwaI restriction endonucleases at MCSI and acts as a "stuffer fragment" to avoid potential interference between STAR elements and adjacent promoters. pIRES-stuf is digested with BglII and FspI to liberate a DNA fragment composed of the stuffer fragment, the CMV promoter, the IRES element (flanked by multiple cloning sites MCS A and MCS B), and the SV40 polyadenylation signal. This fragment is ligated with the vector backbone of pd2EGFP-link produced by digestion with BamHI and StuI to yield pd2IRES-link.

The open reading frames of the zeocin-resistance genes are inserted into the BamHI/NotI sites of MCS B in pd2IRES-link as follows: the zeocin-resistance ORF is amplified by PCR with primers (GATCGGATCCTTCGAAATGGCCAAGTTGACCAGTGC (SEQ ID NO:13)) and (AGGCGCGGCCGCAATTCTCAGTCCTGCTCCTC (SEQ ID NO:14)) from plasmid pEM7/zeo, digested with BamHI and NotI, and ligated with BamHI/NotI-digested pd2IRES-link to yield pd2IRES-link-zeo.

The SEAP reporter ORF is introduced into pd2IRES-link-zeo by PCR amplification of pSEAP2-basic with primers (GATCGAATTCTCGCGACTTCGCCCACCATGC (SEQ ID NO:15)) and (AGGCGAATTCACCGGTGTTTAAACT-CATGTCTGCTCGAAGCGGCCGG (SEQ ID NO:16)), and insertion of the EcoRI-digested SEAP cassette into the EcoRI sites in MCS A of the plasmids pd2IRES-link-zeo (to yield plasmid PP2). PP2 is cut with EcoRI and MluI to remove the SEAP gene and p2EGFP is introduced with primers (GATC-GAATTCATGGTGAGCAAGGGCGAGGAG (SEQ ID NO:17)) and (AGGCACGCGTGTTAACCTACACAT-TGATCCTAGCAGAAGC (SEQ ID NO:18)).

AscI STAR fragments are cloned in to the AscI site of MCS I of ppd2EGFP. A 2.4 kb lambda DNA fragment (TRAP) is amplified using primers (GATCATTTAAATGTCGACCT-GAATTGCTATGTTTAGTGAGTTG (SEQ ID NO: 19)) and (GATCGTCGACGTTTGGCTGATCGGC (SEQ ID NO:20)), and cloned as a SalI fragment in MCS 1,5' to the STAR. STAR and TRAP are then amplified using primers (GATCTTAATTAACCAAGCTTGCATGCCTGCAG (SEQ ID NO:20)) and (AGGCGATATCGCGCGAGACGATT-TAAATGG (SEQ ID NO:21)), cut with EcoRV and PacI, and ligated into the same vector, cut with EcoRV and PacI, from which they were amplified.

Transfection and Culture of CHO Cells

The Chinese Hamster Ovary cell line CHO-K1 (ATCC CCL-61) is cultured in HAMS-F12 medium+10% Fetal Calf Serum containing 2 mM glutamine, 100 U/ml penicillin, and 100 micrograms/ml streptomycin at 37° C./5% $CO_2$. Cells are transfected with the indicated plasmids using SuperFect (QIAGEN) as described by the manufacturer. Briefly, cells are seeded to culture vessels and grown overnight to 70 to 90% confluence. SuperFect reagent is combined with plasmid DNA at a ratio of 6 microliters per microgram (e.g., for a 10 cm Petri dish, 20 micrograms DNA and 120 microliters SuperFect) and added to the cells. After another overnight incubation, zeocin is added to a concentration of 50 μg/ml and the cells are cultured further. After another three days, the medium is replaced by fresh medium containing zeocin (100 μg/ml) and cultured further. When individual colonies become visible (approximately ten days after transfection), medium is removed and replaced with fresh medium without zeocin. Individual clones are isolated and transferred to 24-well plates in medium without zeocin. One day after isolation of the colonies, zeocin is added to the medium. Expression of the GFP reporter gene is assessed approximately three weeks after transfection.

The tested constructs basically consist of a bicistronic gene with the GFP gene, an IRES and the Zeocin-resistance gene under control of the CMV promoter and a monocistronic gene encoding the puromycin-resistance gene under control of the SV40 promoter (FIG. 2A). Diversity in the constructs is created by the addition of the 2400 bp lambda (bp 35711-38103) (Table 1) TRAP to the 5' and 3' ends, STAR40 (Table 2) to the 5' and 3' ends or the combination of STAR40 and the lambda (bp 35711-38103) TRAP to the 5' and 3' ends. The constructs are transfected to CHO-K1 cells. Stable colonies are expanded before the GFP signal is determined on a XL-MCL Beckman Coulter flow cytometer. The mean of the GFP signal is taken as measure for the level of GFP expression and this is plotted in FIG. 5.

Results

FIG. 5 shows that flanking the entire GFP—IRES-Zeo construct (FIG. 2A) with the lambda (bp 35711-38103) TRAP in the 5'-3' orientation (see FIG. 4) does not result in stable CHO colonies that express significantly higher levels of GFP protein, as compared to the "empty" control without the TRAP sequences (Control). However, flanking the entire cassette with the combined lambda (bp 35711-38103) TRAP (5'-3' orientation) and STAR40 results in significantly higher GFP signals (approximately 200%) as compared to the highest GFP signals that are obtained with a construct that is flanked by STAR40 elements alone. It is, therefore, concluded that the lambda (bp 35711-38103) TRAP potentiates the ability of STAR elements to convey higher expression levels to a transgene.

Example 4

The Influence of a TRAP on Protein Yield is Orientation-Dependent

Materials and Methods

The experiments of Example 3 are referred to.

Results

As shown in FIG. 6, the orientation of the TRAP is an essential parameter in the action of TRAP sequences. The phage lambda (bp 35711-37230) TRAP serves only as TRAP in the 5'-3' orientation (FIG. 3, lane 2). When tested in the 3'-5' orientation, which does not convey transcription blocking (FIG. 3, lane 3), no effect on the expression levels of the GFP protein is observed. No effect of the lambda sequence itself is observed and also no effect when combined with STAR40 (FIG. 6). The orientation dependency of TRAP sequences is of importance for the orientation in which they can be used when flanking transgenes.

Example 5

The Stability of Transgene Expression is Improved by TRAPs

During cultivation of recombinant host cells, it is common practice to maintain antibiotic selection. This is intended to prevent transcriptional silencing of the transgene, or loss of the transgene from the genome by processes such as recombination. However, it is undesirable for production of proteins for a number of reasons. First, the antibiotics that are used are quite expensive and contribute significantly to the unit cost of the product. Second, for biopharmaceutical use, the protein must be demonstrably pure, with no traces of the antibiotic in the product. One advantage of STARs and TRAPs for heterologous protein production is that they confer stable expression on transgenes during prolonged cultivation, even in the absence of antibiotic selection; this property is demonstrated in this example.

Materials and Methods

GFP expression levels in the colonies that are described in Example 3 are measured after periods of one week. After the initial three weeks after transfection when the first GFP measurements are performed, the colonies are cultured in medium without zeocin or other antibiotics. This continued for the remainder of the experiment.

Results

FIG. 7 shows the data on GFP expression of colonies that are stably transfected with the GFP construct that is flanked by the combined lambda (bp 35711-38103) TRAP in the 5'-3' orientation and STAR40. The colonies with the highest GFP expression levels in FIG. 5 are chosen for analysis of stability of expression over time in the absence of selection pressure by antibiotics. The expression of the reporter GFP protein remains stable in the CHO cells in three time points. The first time point represents the start of the experiment when the selection pressure is removed. Measurements are performed after one, two and three weeks, which signifies approximately 10, 20 and 30 cell cycles, respectively. Colonies containing the combined Lambda TRAP and STAR40 are stable in the absence of antibiotics. This demonstrates that application of the ability of a combination of TRAPs and STAR elements protect transgenes from silencing during prolonged cultivation. It also demonstrates that this property is independent of antibiotic selection.

Example 6

TRAP Sequences Block Transcription in the Context of STAR Elements

Materials and Methods

Culturing and determination of RNA expression levels are as in Example 1.

Results

The following inserts are placed in the codA constructs:
(1) The empty control vector as shown in FIG. 3;
(2) STAR7;
(3) The SPA/pause sequence in the 5'-3' orientation;
(4) The SPA/pause sequence in the 3'-5' orientation;
(5) The SPA/pause sequence in the 5'-3' orientation and placed 5' of STAR7;
(6) The SPA/pause sequence in the 3'-5' orientation and placed 5' of STAR7;
(7) The SPA/pause sequence in the 5'-3' orientation and placed 3' of STAR7; and
(8) The SPA/pause sequence in the 3'-5' orientation and placed 3' of STAR7.

The eight constructs subsequently transfected to CHO cells, pools of stably transfected colonies are harvested and the codA mRNA levels are measured by Northern blot analysis. The hygromycin-resistance gene is used as internal control, indicating the number of copies of the plasmids. The codA signal is compared to the signal of the empty vector (lane 1).

As shown in FIG. 8, the orientation of the SPA/pause TRAP is an essential parameter in the action of TRAP sequences. The SPA/pause serves only as TRAP in the 5'-3' orientation (lane 3) and not in the 3'-5' orientation (lane 4). The STAR7 does not serve as TRAP (lane 2). When placed 5' of STAR7, the SPA/pause sequence still serves as a TRAP in the 5'-3' orientation (lane 5), but not in the 3'-5' orientation (lane 6). When placed 3' of STAR7, the SPA/pause sequence also serves as a TRAP in the 5'-3' orientation (lane 7), but not in the 3'-5' orientation (lane 8). We conclude that the SPA/pause sequence still functions as TRAP in the context of a STAR element. This is of importance since the TRAP sequence is used in the context of a STAR element when flanking a transgene. We also conclude that the orientation dependency of the TRAP remains the same in the context of the STAR element: only the 5'-3' orientation provides TRAP function. The orientation dependency of TRAP sequences is of importance for the orientation in which they can be used when flanking transgenes. We finally conclude that placing the SPA/pause sequence 5' or 3' of the STAR element does not influence its TRAP function. Only the orientation of the TRAP sequence itself matters.

TABLE 1

TRAP sequences used for testing in the described Examples.

| | |
|---|---|
| Lambda fragment 35711-38103 | (SEQ ID NO: 23) |
| Lambda fragment 22425-27972 | (SEQ ID NO: 24) |
| A combined synthetic polyA (SPA) sequence and a pausing signal from the human α2 globin gene | (SEQ ID NO: 25) |
| Inter histone H3FA-H4F (http://genome.ucsc.edu/cgi-bin/hgTracks?hgsid=13148179&position=chr6%3A26063) (Chromosome 6; bp 26063887-26064766) | (SEQ ID NO: 26) |
| Inter histone H1F4-H2BFB (chr6:26214737-26215909) | (SEQ ID NO: 27) |

TABLE 2

STAR elements used for testing in the described examples.

| | |
|---|---|
| STAR4 | (SEQ ID NO: 28), |
| STAR6 | (SEQ ID NO: 29), |
| STAR7 | (SEQ ID NO: 30), |
| STAR12 | (SEQ ID NO: 31), |
| STAR18 | (SEQ ID NO: 32), |
| STAR35 | (SEQ ID NO: 33), |
| and STAR40 | (SEQ ID NO: 34). |

REFERENCES

Ashfield R., A. J. Patel, S. A. Bossone, H. Brown, R. D. Campbell, K. B. Marcu and N. J. Proudfoot. MAZ-dependent termination between closely spaced human complement genes. *EMBO. J.* 13:5656-5667.

Berger J., J. Hauber, R. Hauber, R. Geiger and B. R. Cullen (1988) Secreted placental alkaline phosphatase: a powerful new quantitative indicator of gene expression in eukaryotic cells. *Gene* 66:1-10.

Boshart M., F. Weber, G. Jahn, K. Dorsch-Hasler, B. Fleckenstein and W. Schaffner (1985) A very strong enhancer is located upstream of an immediate early gene of human cytomegalovirus. *Cell* 41:521-30.

Chad H. E. and S. M. Chamow (2001) Therapeutic antibody expression technology. *Curr. Opin. Biotechn.* 12:188-194.

Das R. C. (2001) Proteins and antibodies make advances as therapeutic products. *Am. Clin. Lab.* 20:8-14.

Chevet E., P. H. Cameron, M. F. Pelletier, D. Y. Thomas and J. J. Bergeron (2001) The endoplasmic reticulum: integration of protein folding, quality control, signaling and degradation. *Curr. Opin. Struct. Biol.* 11:120-4.

Das G. C., S. K. Niyogi and N. P. Salzman (1985) SV40 promoters and their regulation. *Prog. Nucleic Acid Res. Mol. Biol.* 32:217-36.

Eszterhas S. K., E. E. Bouhassira, D. I. Martin and S. Fiering (2002) Transcriptional interference by independently regulated genes occurs in any relative arrangement of the genes and is influenced by chromosomal integration position. *Mol. Cell. Biol.* 22:469-79.

European patent application 01202581.3.

Garrick D., S. Fiering, D. I. Martin and E. Whitelaw (1998) Repeat-induced gene silencing in mammals. *Nat. Genet.* 18:56-9.

Kain S. R. (1997) Use of secreted alkaline phosphatase as a reporter of gene expression in mammalian cells. *Methods Mol. Biol.* 63:49-60.

Kaufman R. J. (2000) Overview of vector design for mammalian gene expression. *Mol. Biotechnol.* 16:151-60.

Kaufman R. J. (1990) Selection and coamplification of heterologous genes in mammalian cells. *Methods in Enzymology* 185:536-566.

Kaufman R. J. and P. A. Sharp (1982) Construction of a modular dihydrofolate reductase cDNA gene: analysis of signals utilized for efficient expression. *Mol. Cell. Biol.* 2:1304-19.

Levitt N., D. Briggs, A. Gil and N. J. Proudfoot (1989) Definition of an efficient synthetic poly(A) site. *Genes and Dev.* 3:1019-1025.

Liu D T. (1992) Glycoprotein pharmaceuticals: scientific and regulatory considerations, and the US Orphan Drug Act. *Trends Biotechnol.* 10:114-20.

Lopez de Quinto S, and E. Martinez-Salas (1998) Parameters influencing translational efficiency in aphthovirus IRES-based bicistronic expression vectors. *Gene* 217:51-6.

Martin D. I. and E. Whitelaw (1996) The vagaries of variegating transgenes. *Bioassays* 18:919-23.

Martinez-Salas E. (1999) Internal ribosome entry site biology and its use in expression vectors. *Curr. Opin. Biotechnol.* 10:458-64.

McBurney M. W., T. Mai, W. Yang and K. Jardine (2002) Evidence for repeat-induced gene silencing in cultured Mammalian cells: inactivation of tandem repeats of transfected genes. *Exp. Cell. Res.* 274:1-8.

Meyer P. (2000) Transcriptional transgene silencing and chromatin components. *Plant Mol. Biol.* 43:221-34.

Migliaccio A. R., C. Bengra, J. Ling, W. Pi, C. Li, S. Zeng, M. Keskintepe, B. Whitney, M. Sanchez, G. Migliaccio and D. Tuan (2000) Stable and unstable transgene integration sites in the human genome: extinction of the Green Fluorescent Protein transgene in K562 cells. *Gene* 256:197-214.

Mizuguchi H., Z. Xu, A. Ishii-Watabe, E. Uchida and T. Hayakawa (2000) IRES-dependent second gene expression is significantly lower than cap-dependent first gene expression in a bicistronic vector. *Mol. Ther.* 1:376-82.

PCT patent application, PCT/NL02/00390.

Rees S., J. Coote, J. Stables, S. Goodson, S. Harris and M. G. Lee (1996) Bicistronic vector for the creation of stable mammalian cell lines that predisposes all antibiotic-resistant cells to express recombinant protein. *Biotechniques* 20:102-4, 106, 108-10.

Sambrook J., E. F. Fritsch and T. Maniatis (1989) *Molecular Cloning: A Laboratory Manual*, Second ed., Cold Spring Harbor Laboratory Press, Plainview N.Y.

Sanger F., S, Nicklen and A. R. Coulson (1977) DNA sequencing with chain-terminating inhibitors. *Proc. Natl. Acad. Sci. U.S.A.* 74:5463-7.

Schorpp M., R. Jager, K. Schellander, J. Schenkel, E. F. Wagner, H. Weiher and P. Angel (1996) The human ubiquitin C promoter directs high ubiquitous expression of transgenes in mice *Nucleic Acids Res.* 24:1787-8.

Sheeley D. M., B. M. Merrill and L. C. Taylor (1997) Characterization of monoclonal antibody glycosylation: comparison of expression systems and identification of terminal alpha-linked galactose. *Anal. Biochem.* 247:102-10.

Stam M., A. Viterbo, J. N. Mol and J. M. Kooter (1998) Position-dependent methylation and transcriptional silencing of transgenes in inverted T-DNA repeats: implications for posttranscriptional silencing of homologous host genes in plants. *Mol. Cell. Biol.* 18:6165-77.

Stam M., R. De Bruin, R. Van Blokland, R. A. L. Ten Hoorn, J. N. Mol and J. M. Kooter (2000) Distinct features of post-transcriptional gene silencing by antisense transgenes in single copy and inverted T-DNA repeat loci. *Plant J.* 21:27-42.

Strutzenberger K., N. Borth, R. Kunert, W. Steinfellner and H. Katinger (1999) Changes during subclone development and ageing of human antibody-producing recombinant CHO cells *J. Biotechnol.* 69:215-26.

Venkatesan A. and A. Dasgupta (2001) Novel fluorescence-based screen to identify small synthetic internal ribosome entry site elements. *Mol. Cell. Biol.* 21:2826-37.

Wright A. and S. L. Morrison (1997) Effect of glycosylation on antibody function: implications for genetic engineering. *Trends Biotechnol.* 15:26-32.

Yang T. T., P. Sinai, P. A. Kitts and S. R. Kain (1997) Quantification of gene expression with a secreted alkaline phosphatase reporter system. *Biotechniques* 23:1110-4.

What is claimed is:

1. A protein expression unit that comprises, functionally linked from 5' to 3':
   i) a promoter;
   ii) an open reading frame encoding a protein of interest; and
   iii) a transcription termination signal;
   wherein the protein expression unit further comprises at least one transcription terminator and/or a polyadenylation signal polynucleotide that is located downstream of the open reading frame and is in a 3' to 5' orientation, and wherein the transcription terminator signal and/or polyadenylation signal polynucleotide is selected from the group consisting of SEQ ID NO:23, SEQ ID NO:24, SEQ ID NO:26, and SEQ ID NO:27.

2. The protein expression unit of claim 1, wherein the protein expression unit further comprises a transcription terminator and/or a polyadenylation signal polynucleotide upstream of the promoter in a 5' to 3' orientation.

3. The protein expression unit of claim 1, wherein the protein expression unit further comprises at least one Stabilizing Anti-Repressor (STAR) polynucleotide selected from the group consisting of SEQ ID NO:28, SEQ ID NO:29, SEQ ID NO:30, SEQ ID NO:31, SEQ ID NO:32, SEQ ID NO:33, SEQ ID NO:34.

4. The protein expression unit of claim 3, comprising in the following order:
   a) one transcription terminator signal and/or a polyadenylation signal polynucleotide in a 5' to 3' orientation;
   b) one STAR sequence;
   c) the combination formed by the promoter, open reading frame and transcription termination signal;
   d) one STAR polynucleotide; and
   e) one transcription terminator signal and/or a polyadenylation signal polynucleotide in a 3' to 5' orientation.

5. The protein expression unit of claim 1, wherein the protein of interest is an immunoglobulin chain.

6. The protein expression unit of claim 1, wherein the open reading frame encoding the protein of interest is in a monocistronic gene.

7. The protein expression unit of claim 1, wherein the open reading frame encoding the protein of interest is in a bicistronic gene with a selection marker.

8. The protein expression unit of claim 7, wherein the bicistronic gene comprises an Internal Ribosome Entry Site located downstream of the open reading frame encoding the protein of interest and upstream of the selection marker.

9. The protein expression unit of claim 1, wherein the promoter is a CMV promoter, an SV40 promoter, a ubiquitin C promoter or a EF1-alpha promoter.

10. A method for expressing at least one protein of interest in a cell comprising providing a cultured cell with at least one protein expression unit that comprises functionally linked from 5' to 3':
    i) a promoter;
    ii) an open reading frame encoding a protein of interest; and
    iii) a transcription termination signal;
    wherein the protein expression unit further comprises at least one transcription terminator and/or a polyadenylation signal polynucleotide that is located downstream of the open reading frame and is in a 3' to 5' orientation; and expressing the protein of interest in the cultured cell, and wherein the transcription terminator and/or polyadenylation signal polynucleotide is selected from the group consisting of SEQ ID NO:23, SEQ ID NO:24, SEQ ID NO:26, and SEQ ID NO:27.

11. The method according to claim 10, wherein the protein expression unit further comprises: a transcription terminator and/or a polyadenylation signal polynucleotide upstream of the promoter in a 5' to 3' orientation.

12. The method according to claim 10, wherein the protein expression unit further comprises at least one Stabilizing Anti-Repressor (STAR) polynucleotide selected from the group consisting of SEQ ID NO:28, SEQ ID NO:29, SEQ ID NO:30, SEQ ID NO:31, SEQ ID NO:32, SEQ ID NO:33, and SEQ ID NO:34.

13. The method according to claim 10, wherein the protein of interest is an immunoglobulin chain.

14. The method according to claim 10, wherein the open reading frame encoding the protein of interest is in a monocistronic gene.

15. The method according to claim 10, wherein the open reading frame encoding the protein of interest is in a bicistronic gene with a selection marker.

16. The method according to claim 15, wherein the bicistronic gene comprises an Internal Ribosome Entry Site located downstream of the open reading frame encoding the protein of interest and upstream of the selection marker.

17. The method according to claim 10, further comprising providing the cell with a second protein expression unit.

18. The method according to claim 17, wherein each of the protein expression units reside on a separate DNA-carrier.

19. An isolated cell comprising at least one protein expression unit of claim 1.

20. The cell of claim 19, which is a plant cell or a mammalian cell.

21. The cell of claim 19, wherein the cell is selected from the group consisting of a U-2 OS osteosarcoma, CHO, 293, HuNS-1 myeloma, WERI-Rb-1 retinoblastoma, BHK, Vero, non-secreting mouse myeloma Sp2/0-Ag 14, non-secreting mouse myeloma NSO, and NCI-H295R adrenal gland carcinoma cell.

22. A method for producing a protein of interest, the method comprising:
    culturing the cell of claim 19 in a culture; and
    harvesting the protein of interest from the culture.

23. A method for expressing a protein of interest in a U2-OS cell comprising:
    providing the cell with at least one monocistronic protein expression unit comprising, functionally linked from 5' to 3',
    i) a CMV promoter;
    ii) an open reading frame encoding a protein of interest;
    iii) a transcription termination signal;
    iv) at least one polynucleotide comprising SEQ ID NO:30; and
    v) a polynucleotide located downstream of the open reading frame in a 3' to 5' orientation, wherein said polynucleotide comprises SEQ ID NO:23; and
    expressing the protein of interest in the cell.

* * * * *